(12) United States Patent
Kiyose

(10) Patent No.: US 9,687,214 B2
(45) Date of Patent: Jun. 27, 2017

(54) ULTRASONIC MEASURING DEVICE, PROGRAM, AND METHOD OF CONTROLLING ULTRASONIC MEASURING DEVICE

(71) Applicant: SEIKO EPSON CORPORATION, Tokyo (JP)

(72) Inventor: Kanechika Kiyose, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 138 days.

(21) Appl. No.: 14/063,662

(22) Filed: Oct. 25, 2013

(65) Prior Publication Data

US 2014/0121522 A1 May 1, 2014

(30) Foreign Application Priority Data

Oct. 30, 2012 (JP) ................................ 2012-238668

(51) Int. Cl.

| | | |
|---|---|---|
| *A61B 8/08* | (2006.01) | |
| *A61B 8/00* | (2006.01) | |
| *A01K 29/00* | (2006.01) | |
| *A61B 5/00* | (2006.01) | |
| *G01N 33/12* | (2006.01) | |

(52) U.S. Cl.
CPC ............ *A61B 8/5207* (2013.01); *A01K 29/00* (2013.01); *A61B 8/085* (2013.01); *A61B 8/0858* (2013.01);
(Continued)

(58) Field of Classification Search
CPC ....... A61B 8/00; A61B 8/5207; A61B 8/0858; A61B 8/4466; A61B 8/5223; A61B 8/54; A61B 8/4494; A61B 8/085; A61B 8/4254; A61B 8/462; A61B 8/465; A61B 8/4427;
(Continued)

(56) References Cited

U.S. PATENT DOCUMENTS 4,511,984 A * 4/1985 Sumino et al. ............... 600/437
5,720,286 A * 2/1998 Chapelon et al. ............ 600/439
(Continued)

FOREIGN PATENT DOCUMENTS

JP 2004-305377 A 11/2004
JP 2005-095221 A 4/2005
(Continued)

*Primary Examiner* — Peter Luong
(74) *Attorney, Agent, or Firm* — Global IP Counselors, LLP

(57) ABSTRACT

An ultrasonic measuring device includes an ultrasonic transducer device, and a processing device that performs processing based on a reception signal from the ultrasonic transducer device. The processing device includes a data acquisition unit that, based on the reception signal, acquires 1st to K-th (K being an integer greater than or equal to 2) A-mode waveform data groups that correspond to cases where the direction of the scanning plane relative to a measurement location surface is 1st to K-th directions; a selection unit that selects a measurement result A-mode waveform data piece based on the 1st to K-th A-mode waveform data groups; and a notification control unit that generates notification data based on the at least one of the measurement result A-mode waveform data piece and a measurement result A-mode waveform data group that corresponds to the measurement result A-mode waveform data piece, and outputs the generated notification data.

17 Claims, 18 Drawing Sheets

(52) U.S. Cl.
CPC .......... *A61B 8/4254* (2013.01); *A61B 8/4427* (2013.01); *A61B 8/4466* (2013.01); *A61B 8/4494* (2013.01); *A61B 8/462* (2013.01); *A61B 8/465* (2013.01); *A61B 8/5223* (2013.01); *A61B 8/54* (2013.01); *A61B 5/4519* (2013.01); *A61B 5/4872* (2013.01); *A61B 8/0875* (2013.01); *A61B 8/4455* (2013.01); *G01N 33/12* (2013.01); *G01N 2291/018* (2013.01)

(58) Field of Classification Search
CPC .......................... A61B 8/4455; A61B 8/0875
USPC .................................................. 600/437, 445
See application file for complete search history.

(56) References Cited

U.S. PATENT DOCUMENTS

| | | | |
|---|---|---|---|
| 6,106,464 A * | 8/2000 | Bass ........................ | A61B 8/00 600/439 |
| 2010/0217125 A1 | 8/2010 | Kadokura et al. | |
| 2011/0144500 A1* | 6/2011 | Nihei et al. .................. | 600/443 |
| 2013/0142010 A1* | 6/2013 | Ajiki ................................. | 367/7 |
| 2013/0150722 A1 | 6/2013 | Kiyose et al. | |
| 2013/0245448 A1 | 9/2013 | Kadokura et al. | |

FOREIGN PATENT DOCUMENTS

| | | |
|---|---|---|
| JP | 2005-288043 A | 10/2005 |
| JP | 2006-095151 A | 4/2006 |
| JP | 2009-160370 A | 7/2009 |
| JP | 2013-123459 A | 6/2013 |

* cited by examiner

B MODE IMAGE

B MODE IMAGE

MEASUREMENT RESULT

| SITE | BACK OF ARM |
|---|---|
| FAT THICKNESS | 6.8 |
| STANDARD VALUE | 6.2 |
| MUSCLE THICKNESS | 29.2 |
| STANDARD VALUE | 30.3 |

FIG. 8

ULTRASONIC MEASURING DEVICE, PROGRAM, AND METHOD OF CONTROLLING ULTRASONIC MEASURING DEVICE

CROSS REFERENCE TO RELATED APPLICATIONS

This application claims priority to Japanese Patent Application No. 2012-238668, filed Oct. 30, 2012. The entire disclosure of Japanese Patent Application No. 2012-238668 is expressly incorporated by reference herein.

BACKGROUND

1. Technical Field

The present invention relates to an ultrasonic measuring device, a program, a method of controlling the ultrasonic measuring device, and the like.

2. Related Art

As one example of a device that emits ultrasonic waves toward an object and receives reflected waves from interfaces between materials that have different acoustic impedances inside the object, there is known to be an ultrasonic measuring device for examining the inside of a human body that is the test subject, for example. In typical ultrasonic measuring devices, an ultrasonic probe and a display unit for displaying measurement results are accommodated in separate housings.

Meanwhile, applications of ultrasonic measuring devices include the measurement of visceral fat, the measurement of blood flow, and the like, and there is hope for such applications to be expanded to the healthcare field, in which the surface of the test subject is subjected to diagnostic image. In the healthcare field, there is desire to achieve a more compact device size by integrating the ultrasonic probe and the display unit.

Envision a scenario in which the user presses the ultrasonic probe against his or her own body to measure biological information. Depending on the measurement site, the user may possibly need to perform measurement while pressing the ultrasonic probe against a site on his or her body while not being able to view the screen of the display unit. This leads to the risk that the orientation of the scanning plane of the ultrasonic beam will deviate from the ideal orientation, and it will not be possible to obtain correct measurement results. This is a significant problem in the case of ultrasonic measuring devices provided with an integrated display unit, for example. Even in the case of ultrasonic measuring devices whose display unit is not integrated, the operator needs to appropriately adjust measurement conditions such as the direction of the scanning plane of the ultrasonic beam while viewing images on the display unit in order to perform appropriate measurement, and this is problematic in that the measurement operation is not simple. Examples of technology related to ultrasonic measuring devices include the technology disclosed in JP-A-2006-95151.

JP-A-2006-95151 is an example of related art.

SUMMARY

According to some aspects of the invention, it is possible to provide an ultrasonic measuring device, a program, and a method of controlling the ultrasonic measuring device that enable an improvement in user operability and user-friendliness by notifying the user of appropriate measurement results.

A first aspect of the invention is related to an ultrasonic measuring device including: an ultrasonic transducer device that emits an ultrasonic beam while scanning along a scanning plane, and receives an ultrasonic echo resulting from the ultrasonic beam; and a processing device that performs processing based on a reception signal from the ultrasonic transducer device, wherein the processing device includes: a data acquisition unit that, based on the reception signal, acquires 1st to K-th (K being an integer greater than or equal to 2) A-mode waveform data groups that correspond to cases where the direction of the scanning plane of the ultrasonic transducer device relative to a measurement location surface is 1st to K-th directions; a selection unit that selects a measurement result A-mode waveform data piece based on the 1st to K-th A-mode waveform data groups; and a notification control unit that generates notification data based on at least one of the measurement result A-mode waveform data piece that was selected and a measurement result A-mode waveform data group that corresponds to the measurement result A-mode waveform data piece, and outputs the generated notification data.

According to the first aspect of the invention, the 1st to K-th A-mode waveform data groups that correspond to cases where the direction of the scanning plane of the ultrasonic transducer relative to the measurement location surface is the 1st to K-th directions are acquired based on reception signals from the ultrasonic transducer device that successively emits an ultrasonic beam along the scanning plane. For example, the 1st to K-th A-mode waveform data groups are the data groups that are acquired due to the ultrasonic beam being scanned when the scanning plane direction is each of the 1st to K-th directions. Then, in accordance with a predetermined determination criterion for example, an appropriate measurement result A-mode waveform data piece is selected based on the 1st to K-th A-mode waveform data groups that were acquired, notification data is generated based on that measurement result A-mode waveform data piece, and the user is informed of the notification data by the notification unit. This enables informing the user of appropriate measurement results, and enables improving user operability, user-friendliness, and the like.

Also, in the first aspect of the invention, in a case where the selection unit selected an A-mode waveform data piece corresponding to a case where the direction of the scanning plane is an L-th ($1 \leq L \leq K$) direction as the measurement result A-mode waveform data piece, the notification control unit may generate the notification data based on at least one of the measurement result A-mode waveform data piece and the measurement result A-mode waveform data group that were acquired when the direction of the scanning plane was the L-th direction, and output the generated notification data.

According to this configuration, an A-mode waveform data piece that was acquired when the direction of the scanning plane was the L-th direction is selected as the measurement result A-mode waveform data piece, and the notification data is generated based on at least one of the measurement result A-mode waveform data piece that was selected and the measurement result A-mode waveform data group that corresponds to the selected measurement result A-mode waveform data piece. Accordingly, an A-mode waveform data piece that was acquired at an appropriate scanning plane direction is automatically selected, and the user can be informed of the corresponding measurement results or the like.

Also, in the first aspect of the invention, the notification control unit may generate a B-mode image as the notification data based on the measurement result A-mode waveform data group that was acquired when the direction of the scanning plane was the L-th direction, and output the generated B-mode image.

According to this configuration, a B-mode image that corresponds to the case where the scanning plane direction was the L-th direction when the measurement result A-mode waveform data piece was selected can be displayed on a display unit as a measurement result image.

Also, in the first aspect of the invention, the notification control unit may generate, as the notification data, an image including a number, a character, or a symbol expressing an ultrasonic measurement result that was obtained when the direction of the scanning plane was the L-th direction, or audio expressing the ultrasonic measurement result, and output the image or the audio that was generated.

According to this configuration, the user can be informed of an image including numbers, characters, or symbols expressing ultrasonic measurement results that correspond to the case where the scanning plane direction was the L-th direction when the measurement result A-mode waveform data piece was selected, or can be informed of audio expressing those ultrasonic measurement results.

Also, in the first aspect of the invention, the selection unit may obtain 1st to K-th A-mode waveform data pieces from the 1st to K-th A-mode waveform data groups, and from among the 1st to K-th A-mode waveform data pieces that were obtained, select an A-mode waveform data piece in which the amplitude at a peak waveform of interest is highest as the measurement result A-mode waveform data piece.

According to this configuration, the A-mode waveform data piece in which the amplitude at the peak waveform of interest is the highest is searched for from among the 1st to K-th A-mode waveform data pieces that were obtained from the 1st to K-th A-mode waveform data groups, and thus the user can be informed of measurement results or the like that correspond to the case where the scanning plane direction was an appropriate direction.

Also, in the first aspect of the invention, the notification control unit may generate a B-mode image as the notification data based on the measurement result A-mode waveform data group that corresponds to the measurement result A-mode waveform data piece that was selected, and output the generated B-mode image.

According to this configuration, when the measurement result A-mode waveform data piece is selected from among the 1st to K-th A-mode waveform data pieces based on a predetermined determination criterion for example, a B-mode image is generated based on the measurement result A-mode waveform data group that corresponds to the measurement result A-mode waveform data piece, and the B-mode image is displayed.

Also, in the first aspect of the invention, the selection unit may obtain the 1st to K-th A-mode waveform data pieces from the 1st to K-th A-mode waveform data groups by performing averaging processing for each of the 1st to K-th A-mode waveform data groups or performing selection processing for selecting a representative A-mode waveform data piece from each of the 1st to K-th A-mode waveform data groups.

According to this configuration, it is possible to obtain the 1st to K-th A-mode waveform data pieces by performing averaging processing or selection processing on the 1st to K-th A-mode waveform data groups, and select an measurement result A-mode waveform data piece from among the 1st to K-th A-mode waveform data pieces that were obtained.

Also, in the first aspect of the invention, the selection unit may perform processing for comparing the amplitude at the peak waveform of interest in an M-th ($1 \leq M < K$) A-mode waveform data piece obtained from an M-th A-mode waveform data group from among the 1st to K-th A-mode waveform data groups with the amplitude at the peak waveform of interest in an (M+1)-th A-mode waveform data piece obtained from an (M+1)-th A-mode waveform data group, and for, out of the M-th A-mode waveform data piece and the (M+1)-th A-mode waveform data piece, selecting and saving the one A-mode waveform data piece for which it was determined that the amplitude at the peak waveform of interest is higher, and deleting the other A-mode waveform data piece and the A-mode waveform data group that corresponds to the other A-mode waveform data piece.

According to this configuration, it is possible to save the one A-mode waveform data piece that has the higher amplitude at the peak waveform of interest, and delete the other A-mode waveform data piece having the smaller amplitude along with the corresponding A-mode waveform data group. This enables selecting an appropriate measurement result A-mode waveform data piece while also reducing the amount of storage that is used, for example.

Also, in the first aspect of the invention, the ultrasonic measuring device may include: a correlation data storage unit that stores correlation data that represents a correlation between the amplitude of the A-mode waveform and depth, wherein the selection unit may select, as the measurement result A-mode waveform data piece, an A-mode waveform data piece for which it was determined that the correlation between the amplitude at the peak waveform of interest and the depth is appropriate based on the correlation data.

According to this configuration, it is possible to determine whether or not the correlation between the amplitude of the A-mode waveform and the depth is appropriate based on correlation data, and select a measurement result A-mode waveform data piece from among A-mode waveform data pieces in which the correlation between amplitude and depth is appropriate.

Also, in the first aspect of the invention, the ultrasonic measuring device may include: a reference data storage unit that stores reference A-mode waveform data for a test subject that is to be subjected to ultrasonic measurement, wherein the selection unit may obtain 1st to K-th A-mode waveform data pieces from the 1st to K-th A-mode waveform data groups, perform comparison processing for comparing each of the 1st to K-th A-mode waveform data pieces that were obtained with the reference A-mode waveform data stored in the reference data storage unit, and select the measurement result A-mode waveform from among the 1st to K-th A-mode waveform data pieces.

According to this configuration, reference A-mode waveform data that is to be a measurement reference is prepared in advance and stored in the reference data storage unit, thus making it possible to select a measurement result A-mode waveform data piece in accordance with the reference A-mode waveform data, generate notification data that corresponds to the selected measurement result A-mode waveform data piece, and inform the user of the notification data.

Also, in the first aspect of the invention, from among the 1st to K-th A-mode waveform data pieces, the selection unit may select an A-mode waveform data piece in which the amplitude at the peak waveform of interest is closest to the amplitude at the peak waveform of interest in the reference A-mode waveform data as the measurement result A-mode waveform data piece.

According to this configuration, it is possible to select an appropriate measurement result A-mode waveform data piece in which the waveform closely resembles the waveform in the reference A-mode waveform data, generate notification data that corresponds to that measurement result A-mode waveform data piece, and inform the user of the notification data.

Also, in the first aspect of the invention, the ultrasonic measuring device may include: a guidance instruction unit that performs guidance instruction processing for giving a user who is the test subject guidance instruction regarding the direction of the scanning plane of the ultrasonic transducer device.

According to this configuration, the user is given guidance instruction so as to cause the direction of the scanning plane of the ultrasonic transducer device to be an appropriate direction, and the user changes the direction of the scanning plane in accordance with the guidance instruction, thus making it possible for the A-mode waveform data piece that was acquired at the appropriate scanning plane direction to be selected as the measurement result A-mode waveform data piece.

Also, in the first aspect of the invention, the ultrasonic measuring device may include: a motion sensor that detects motion of the user, wherein the guidance instruction unit may perform the guidance instruction processing regarding the direction of the scanning plane based on a motion detection signal from the motion sensor.

According to this configuration, it is possible to use the motion detection signal from the motion sensor in order to give the user guidance instruction so as to cause the direction of the scanning plane of the ultrasonic transducer device to be an appropriate direction.

Also, in the first aspect of the invention, the ultrasonic measuring device may include: a direction control unit that performs direction control for changing the direction of the scanning plane of the ultrasonic transducer device, wherein the data acquisition unit may acquire the 1st to K-th A-mode waveform data groups that are obtained as the direction of the scanning plane of the ultrasonic transducer device is changed in accordance with the direction control performed by the direction control unit.

According to this configuration, it is possible to change the direction of the scanning plane of the ultrasonic transducer device in accordance with the direction control performed by the direction control unit, and acquire the 1st to K-th A-mode waveform data groups that are obtained as the direction is changed. It is then possible to inform the user of the corresponding appropriate measurement results or the like by selecting a measurement result A-mode waveform data piece based on the 1st to K-th A-mode waveform data groups.

Also, a second aspect of the invention is related to a program for performing processing based on a reception signal from an ultrasonic transducer device that emits an ultrasonic beam while scanning along a scanning plane and receives an ultrasonic echo resulting from the ultrasonic beam, the program causing a computer to function as: a data acquisition unit that, based on the reception signal, acquires 1st to K-th (K being an integer greater than or equal to 2) A-mode waveform data groups that correspond to cases where the direction of the scanning plane of the ultrasonic transducer device relative to a measurement location surface is 1st to K-th directions; a selection unit that selects a measurement result A-mode waveform data piece based on the 1st to K-th A-mode waveform data groups; and a notification control unit that generates notification data based on at least one of the measurement result A-mode waveform data piece that was selected and a measurement result A-mode waveform data group that corresponds to the measurement result A-mode waveform data piece, and outputs the generated notification data.

Also a third aspect of the invention is related to a method of controlling an ultrasonic measuring device for performing processing based on a reception signal from an ultrasonic transducer device that emits an ultrasonic beam while scanning along a scanning plane and receives an ultrasonic echo resulting from the ultrasonic beam, the method including: acquiring, based on the reception signal, 1st to K-th (K being an integer greater than or equal to 2) A-mode waveform data groups that correspond to cases where the direction of the scanning plane of the ultrasonic transducer device relative to a measurement location surface is 1st to K-th directions; selecting a measurement result A-mode waveform data piece based on the 1st to K-th A-mode waveform data groups; and generating notification data based on at least one of the measurement result A-mode waveform data piece that was selected and a measurement result A-mode waveform data group that corresponds to the measurement result A-mode waveform data piece, and outputting the generated notification data.

BRIEF DESCRIPTION OF THE DRAWINGS

FIG. 8 shows an example of a measurement result image, which is a displayed image including numbers or the like expressing ultrasonic measurement results.

DESCRIPTION OF EXEMPLARY EMBODIMENTS

The following is a detailed description of preferred embodiments of the invention. Note that the embodiments described below are not intended to unduly limit the content of the invention recited in the claims, and all of the configurations described in the embodiments are not necessarily essential as solutions provided by the invention.

1. Ultrasonic Measuring Device

Figure 1:
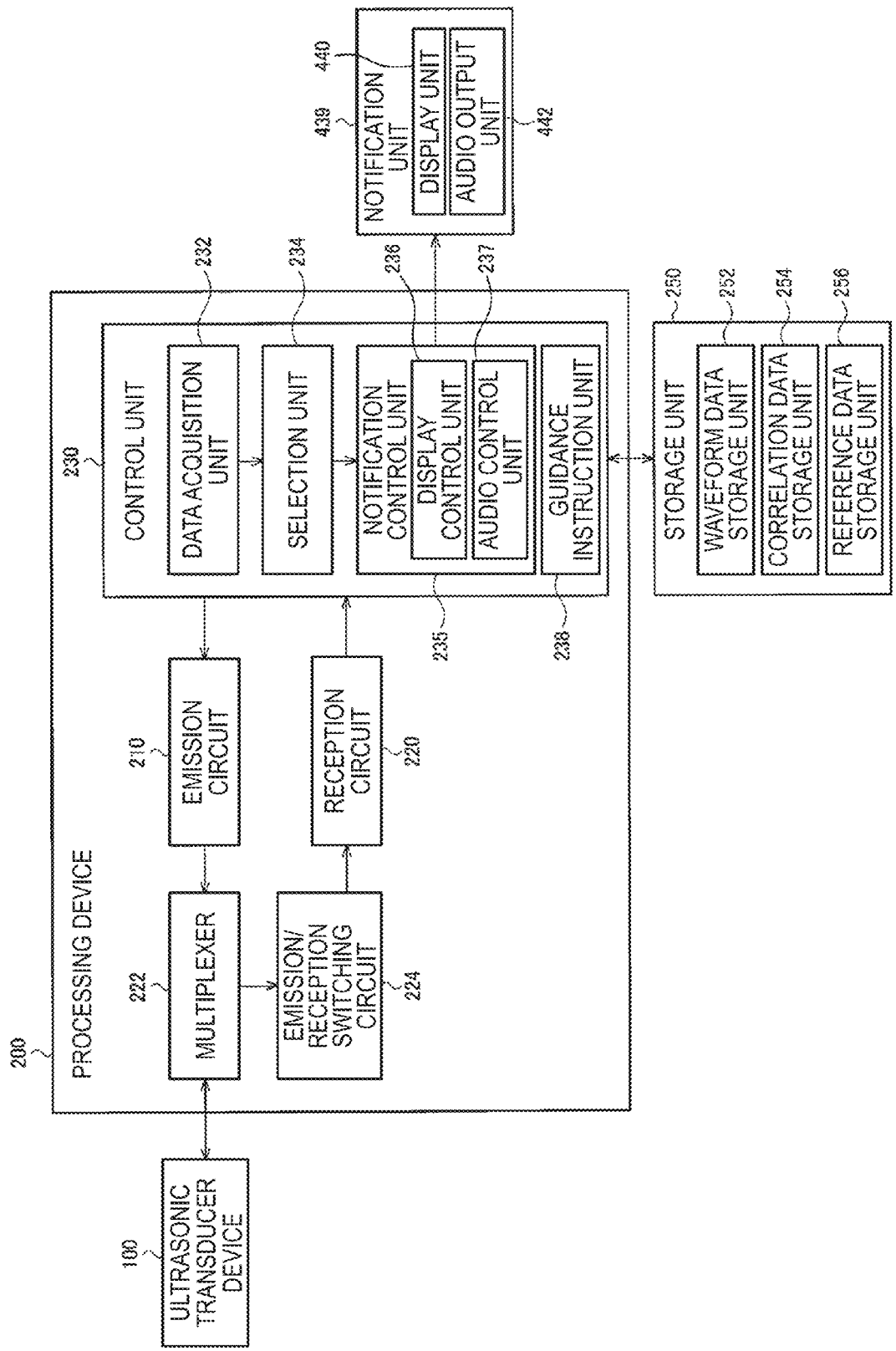
FIG. 1 shows an example of the configuration of an ultrasonic measuring device according to an embodiment.

FIG. 1 shows an example of the configuration of an ultrasonic measuring device (ultrasonic diagnosis device) according to an embodiment. This ultrasonic measuring device includes an ultrasonic transducer device 100 and a processing device 200. It can also include a storage unit 250 and a notification unit 439. Note that the ultrasonic measuring device of this embodiment is not limited to the configuration shown in FIG. 1, and various modifications can be carried out, such as omitting some of the constituent elements, replacing some of the constituent elements with other constituent elements, and adding other constituent elements.

The ultrasonic transducer device 100 emits an ultrasonic beam while scanning along a scanning plane, and also receives an ultrasonic echo resulting from the ultrasonic beam. Taking the example a type of device in which piezoelectric elements are used, the ultrasonic transducer device 100 has multiple ultrasonic transducer elements (an ultrasonic element array) and a substrate in which multiple openings are arranged in an array. Each of the ultrasonic transducer elements has a vibrating membrane that covers a corresponding opening, and a piezoelectric element unit that includes a lower electrode, an upper electrode, and a piezoelectric film that are provided on the vibrating membrane. Details of the ultrasonic transducer device 100 will be described later. Note that a type of transducer that employs the piezoelectric elements (thin-film piezoelectric elements) described in detail later can be applied as the ultrasonic transducer device 100, but this embodiment is not limited to using such a transducer. For example, a type of transducer that employs capacitive elements such as c-MUTs (Capacitive Micro-machined Ultrasonic Transducers) may be applied, or a bulk-type transducer may be applied.

The processing device 200 performs various types of control processing with respect to the ultrasonic measuring device, emission processing and reception processing with respect to the ultrasonic transducer device 100, and the like. This processing device 200 includes an emission circuit 210, a reception circuit 220, a multiplexer 222, an emission/reception switching circuit 224, and a control unit 230. Note that various modifications can be carried out, such as omitting some of the constituent elements, replacing some of the constituent elements with other constituent elements, and adding other constituent elements.

The emission circuit 210 outputs an emission signal to the ultrasonic transducer device 100 via the multiplexer 222. Specifically, in an emission period, the emission circuit 210 generates an emission signal under control of the control unit 230, and outputs the emission signal to the multiplexer 222. This emission circuit 210 can be constituted by, for example, a pulser that outputs an ultrasonic pulse signal.

The multiplexer 222 (selection circuit) selects at least one of the driving electrode lines (channels) of the ultrasonic transducer device 100 under control of the control unit 230, and an emission signal is output from the emission circuit 210 to the selected driving electrode lines. For example, if the multiplexer 222 has selected the first driving electrode line, an emission signal is output to the first driving electrode line in the emission period. Note that the multiplexer 222 may select multiple (n) driving electrode lines (multiple channels) all at the same time, or may successively select a predetermined number of lines at a time.

The reception circuit 220 performs reception processing for receiving a reception signal (echo signal) from the ultrasonic transducer device 100. Specifically, the reception circuit 220 receives a reception signal from the ultrasonic transducer device 100 via the multiplexer 222 and the emission/reception switching circuit 224, and performs reception processing such as reception signal amplification, gain setting, frequency setting, and A/D conversion. The result of the reception processing is input to the control unit 230 as detection data (detection information). This reception circuit 220 is constituted by a low-noise amplifier, a voltage-controlled attenuator, a programmable gain amplifier, a low-pass filter, and an A/D converter, for example.

The emission/reception switching circuit 224 is constituted by multiple (n) switch elements, and performs switching between the emission signal and the reception signal under control of the control unit 230. Specifically, by setting the switch elements to the off state in the emission period, the emission signal output from the emission circuit 210 is prevented from being input to the reception circuit 220. On the other hand, by setting the switch elements to the on state in the reception period, the reception signal from the ultrasonic transducer device 100 is allowed to be input to the reception circuit 220.

The control unit 230 controls the emission circuit 210, the reception circuit 220, the multiplexer 222, and the emission/reception switching circuit 224. For example, the control unit 230 performs control on the emission circuit 210 with respect to the emission signal generation and output processing, and performs control on the reception circuit 220 with respect to reception signal frequency setting, gain, and the like.

The storage unit 250 stores various types of data, and is realized by a RAM, an HDD (Hard Disk Drive), or the like. The storage unit 250 includes a waveform data storage unit 252, a correlation data storage unit 254, and a reference data storage unit 256.

In the present embodiment, the control unit 230 (processing device 200) includes a data acquisition unit 232, a selection unit 234, a notification control unit 235, and a guidance instruction unit 238.

The notification control unit 235 generates and outputs notification data. It also causes the notification unit 439 to perform notification of notification data (measurement results). For example, it switches on the notification unit 439 and causes it to output notification data. The notification control unit 235 includes a display control unit 236 and an audio control unit 237, for example. The display control unit 236 of the notification control unit 235 performs display control with respect to a display unit 440 of the notification unit 439, and causes the display unit 440 to display an image representing measurement results, which is the notification data. The audio control unit 237 performs control with respect to an audio output unit 442 of the notification unit 439, and causes the audio output unit 442 to output audio representing measurement results, which is the notification data.

The notification unit 439 notifies the user (measurer) of measurement results, and is realized by the display unit 440 and the audio output unit 442, for example. The notification unit 439 may be an apparatus that the ultrasonic measuring device has, or may be an apparatus that is separate from the ultrasonic measuring device (e.g., an external display). Various types of displays can be envisioned for the display unit 440, such as a liquid crystal display or an organic EL display. A speaker or the like can be envisioned for the audio output unit 442.

Figure 15:
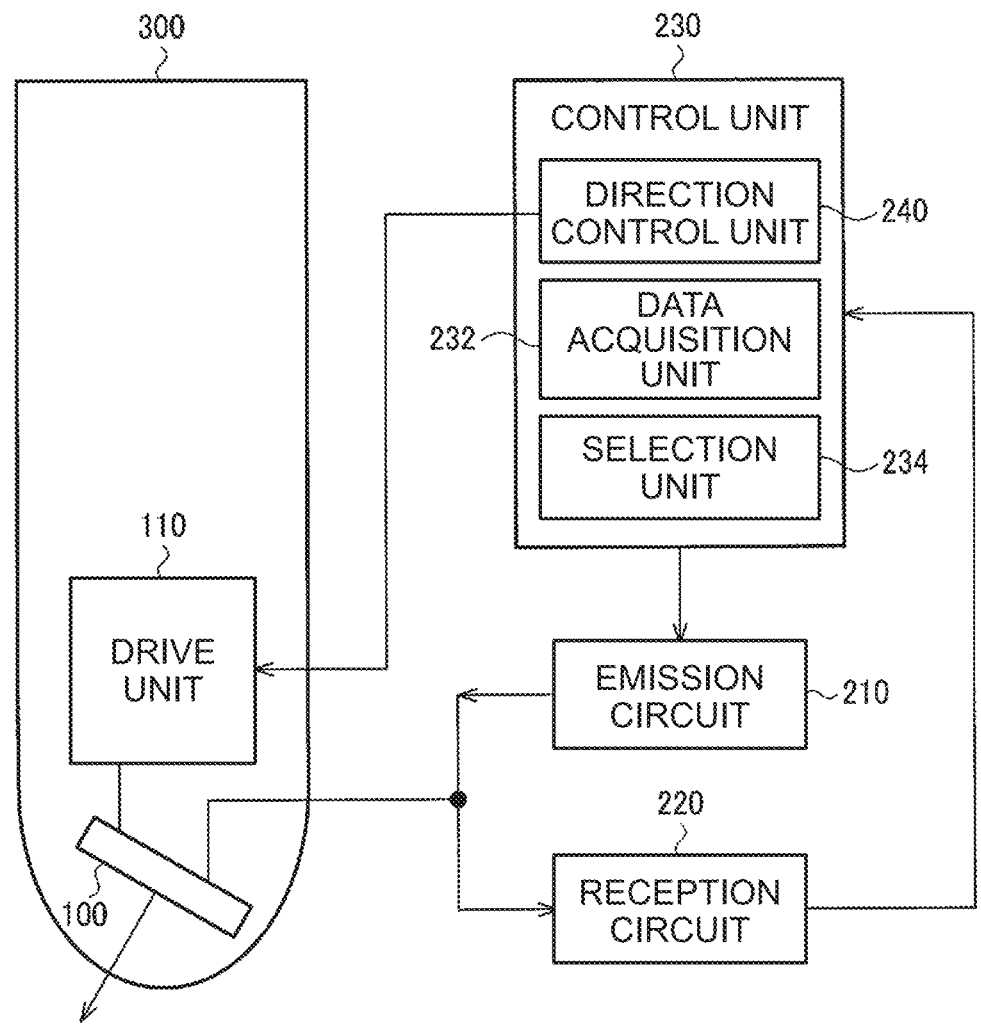
FIG. 15 is a diagram illustrating a procedure for controlling the direction of the scanning plane of the ultrasonic beam of an ultrasonic transducer device.

The data acquisition unit 232 acquires, based on the reception signal from the ultrasonic transducer device 100, 1st to K-th A-mode waveform data groups for the cases where the direction of the scanning plane of the ultrasonic transducer device 100 relative to the measurement location surface is 1st to K-th (K being an integer greater than or equal to 2) directions. For example, if the user swings the ultrasonic probe, or a later-described direction control unit 240 controls the direction of the scanning plane as shown in FIG. 15 in the measurement period, the direction of the scanning plane of the ultrasonic beam relative to the measurement location surface will change. In this period in which the scanning plane direction changes, the data acquisition unit 232 acquires the 1st to K-th A-mode data waveform groups (plurality of A-mode waveform data groups) based on the reception signal from the reception circuit 220. The acquired A-mode waveform data groups are saved by being stored in the waveform data storage unit 252.

The measurement location surface referred to here is the surface at the measurement location against which the ultrasonic probe is pressed, for example, and is the surface of an object such as a body. In the case where the ultrasonic transducer device 100 emits (generates) multiple ultrasonic beams while performing scanning such as linear scanning or sector scanning, the scanning plane is the plane that the ultrasonic beams conform to, for example. The direction of the scanning plane of the ultrasonic beam relative to the measurement location surface is the relative direction (angle) of the scanning plane with the measurement location surface serving as the reference.

The ultrasonic transducer device 100 receives an emission signal, which is an electrical signal (voltage signal), from the emission circuit 210, converts the emission signal into an ultrasonic wave, and emits (outputs) an ultrasonic beam. Upon receiving an ultrasonic echo resulting from the ultrasonic beam, the ultrasonic transducer device 100 converts the ultrasonic echo into a reception signal, which is an electrical signal (voltage signal). The data acquisition unit 232 acquires an A-mode waveform data group based on this reception signal. Each A-mode waveform data group is a group of A-mode waveform data pieces obtained by a respective scan of the ultrasonic transducer device 100, for example. For example, the 1st A-mode waveform data group is acquired by the first scan, the second A-mode waveform data group is acquired by the second scan, and so on, and the K-th A-mode waveform data group is acquired by the K-th scan.

The selection unit 234 selects a measurement result A-mode waveform data piece based on the 1st to K-th A-mode waveform data groups acquired by the data acquisition unit 232. For example, the selection unit 234 obtains 1st to K-th A-mode waveform data pieces from the 1st to K-th A-mode waveform data groups. Specifically, the selection unit 234 obtains the 1st to K-th A-mode waveform data pieces from the 1st to K-th A-mode waveform data groups by performing averaging processing for averaging each A-mode waveform data group among the 1st to K-th A-mode waveform data groups or selection processing for selecting a representative A-mode waveform data piece from each A-mode waveform data group. For example, the A-mode waveform data piece corresponding to a certain A-mode waveform data group is obtained by performing processing for obtaining the average value of the amplitude at each depth, for example, in the A-mode waveform data pieces that belong to that A-mode waveform data group. Alternatively, the A-mode waveform data piece corresponding to a certain A-mode waveform data group is obtained through processing in which, from among the A-mode waveform data pieces that belong to that A-mode waveform data group, a A-mode waveform data piece that is based on the reception signal from a group of elements at a predetermined position (e.g., the central position) in the ultrasonic transducer device 100 is selected as the representative A-mode waveform data piece.

The selection unit 234 then selects a measurement result A-mode waveform data piece from among the obtained 1st to K-th A-mode waveform data pieces based on a predetermined determination criterion. The predetermined determination criterion is a reference for selecting an A-mode waveform data piece that is appropriate for use as a measurement result. Specifically, from among the obtained 1st to K-th A-mode waveform data pieces, the A-mode waveform data piece that has the highest amplitude at the peak waveform of interest is selected by the selection unit 234 as the measurement result A-mode waveform data piece. The peak waveform of interest is the peak waveform that is envisioned to be the peak waveform that is suited to the selection of the measurement result A-mode waveform data piece from among the peak waveforms that appear in an A-mode waveform, and is, for example, the peak waveform that corresponds to the body tissue of interest, such as a bone.

For example, among the 1st to K-th A-mode waveform data groups, the selection unit 234 compares the amplitude at the peak waveform of interest in the M-th (1≤M<K) A-mode waveform data piece obtained from the M-th A-mode waveform data group with the amplitude at the peak waveform of interest in the (M+1)-th A-mode waveform data piece obtained from the (M+1)-th A-mode waveform data group. Then, between the M-th A-mode waveform data piece and the (M+1)-th A-mode waveform data piece, the one A-mode waveform data piece that was determined to have the higher amplitude at the peak waveform of interest is selected and saved. Specifically, it is saved by being stored in the waveform data storage unit 252. Processing is then performed in order to delete the other A-mode waveform data piece and the A-mode waveform data group that corresponds to the other A-mode waveform data piece.

The notification control unit 235 generates notification data based on at least one of the measurement result A-mode waveform data piece that was selected and the measurement result A-mode waveform data group that corresponds to that measurement result A-mode waveform data piece, and outputs the generated notification data. For example, it outputs the notification data by performing notification control with respect to the notification unit 439. Specifically, a measurement result image or measurement result audio representing the notification data is output by the display control unit 236 of the notification control unit 235 performing display control with respect to the display unit 440 or the audio control unit 237 of the notification control unit 235 performing audio control with respect to the audio output unit 442.

Here, the measurement result A-mode waveform data group that corresponds to the measurement result A-mode waveform data piece is, in the case where the selection unit 234 has selected a measurement result A-mode waveform data piece, for example, the A-mode waveform data group that was used in the generation of that measurement result A-mode waveform data piece (generation by averaging processing or selection processing).

For example, take the case where the A-mode waveform data piece that was acquired when the direction of the scanning plane was the L-th (1≤L≤K) direction (i.e., the L-th A-mode waveform data piece) is selected by the selection unit 234 as the measurement result A-mode waveform data piece. In this case, the notification control unit 235 generates the notification data based on at least one of the measurement result A-mode waveform data piece and the measurement result A-mode waveform data group that were acquired when the direction of the scanning plane was the L-th direction. The generated notification data (image, audio) is then output.

For example, the notification control unit 235 (display control unit 236) generates a B-mode image as the notification data based on the measurement result A-mode waveform data group that was acquired when the direction of the scanning plane was the L-th direction, and performs control for displaying the generated B-mode image on the display unit 440, which is the notification unit 439. Take the case where, for example, the 1st to K-th A-mode waveform data pieces are obtained from the 1st to K-th A-mode waveform data groups, and the A-mode waveform data piece having the highest amplitude at the peak waveform of interest is selected as the measurement result A-mode waveform data piece from among the 1st to K-th A-mode waveform data pieces. In this case, the notification control unit 235 generates a B-mode image as the notification data based on the measurement result A-mode waveform data group that corresponds to the measurement result A-mode waveform data piece that was selected, and outputs the generated B-mode image. For example, control is performed for displaying the B-mode image on the display unit 440. For example, the B-mode image is generated by converting the amplitudes of the A-mode waveform data pieces in the measurement result A-mode waveform data group into luminance values, and then control is performed for displaying the B-mode image on the display unit 440.

Note that the notification data in the present embodiment is not limited to being a B-mode image, and various types of notification data can be envisioned. For example, an image including numbers, characters, or symbols expressing ultrasonic measurement results that were acquired when the direction of the scanning plane was the L-th direction, or audio expressing the ultrasonic measurement results is generated as notification data and output by the notification control unit 235. For example, control is performed such that the notification unit 439 notifies the user of the generated image or audio. Specifically, control is performed such that the generated image is displayed on the display unit 440, or the generated audio is output by the audio output unit 442. More specifically, control is performed so as to display an image including numbers, characters, or symbols expressing ultrasonic measurement results such as the measured fat thickness, muscle thickness, or the like of the user, or so as to read aloud the ultrasonic measurement results.

Also, in the present embodiment, correlation data representing the correlation between amplitude in an A-mode waveform and depth is stored in the correlation data storage unit 254 in correspondence with the measurement location, for example. Then, an A-mode waveform data piece for which it was determined that the correlation between the amplitude at the peak waveform of interest and the depth is appropriate based on the correlation data is selected by the selection unit 234 as the measurement result A-mode waveform data piece. For example, the selection unit 234 selects a measurement result A-mode waveform data piece from among multiple A-mode waveform data pieces (1st to K-th A-mode waveform data pieces) that were determined to be appropriate based on the correlation data.

The reference data storage unit 256 stores reference A-mode waveform data for the test subject (user, animal, etc.) that is to be subjected to ultrasonic measurement. The reference A-mode waveform data is data that is, for example, measured in advance as A-mode waveform data that is to serve as the reference for the ultrasonic measurement of a test subject, and is stored in the reference data storage unit 256. The selection unit 234 performs comparison processing for comparing multiple A-mode waveform data pieces acquired by ultrasonic measurement with the reference A-mode waveform data stored in the reference data storage unit 256, and selects a measurement result A-mode waveform data piece from among the A-mode waveform data pieces. Specifically, the selection unit 234 obtains 1st to K-th A-mode waveform data pieces from the 1st to K-th A-mode waveform data groups by performing the above-described averaging processing or selection processing, for example. Comparison processing is then performed in order to compare the 1st to K-th A-mode waveform data pieces that were obtained with the reference A-mode waveform data stored in the reference data storage unit 256, and a measurement result A-mode waveform data piece is selected from among the 1st to K-th A-mode waveform data pieces. For example, from among the 1st to K-th A-mode waveform data pieces, the A-mode waveform data piece whose amplitude at the peak waveform of interest is closest to the amplitude at the peak waveform of interest in the reference A-mode waveform data is selected as the measurement result A-mode waveform data piece.

The guidance instruction unit 238 performs guidance instruction processing for giving the user, who is the test subject, guidance instruction regarding the direction of the scanning plane of the ultrasonic transducer device 100. Specifically, guidance information such as an image or audio is used to instruct the user regarding the direction of the scanning plane of the ultrasonic beam at which appropriate measurement results can be obtained. For example, the ultrasonic measuring device of the present embodiment can be provided with a motion sensor that detects user motion, as will be described later. The motion sensor is an acceleration sensor, a gyro sensor, or the like. The guidance instruction unit 238 performs guidance instruction processing regarding the direction of the scanning plane based on a motion detection signal from the motion sensor. Specifically, the guidance instruction unit 238 detects movement of the ultrasonic probe based on the motion detection signal, and performs guidance instruction processing for causing the user to orient the direction of the scanning plane of the ultrasonic beam in the appropriate direction.

Note that at least a portion of the processing performed by the ultrasonic measuring device of the present embodiment may be realized by a program. In this case, the processing performed by the ultrasonic measuring device of the present embodiment is realized by a processor such as a CPU executing the program. Specifically, a program stored on an information storage medium is read out, and the read-out program is executed by the processor such as the CPU. The information storage medium (computer-readable medium) referred to here can store programs, data, and the like, and the functionality thereof is realized by an HDD (Hard Disk Drive), an optical disk (DVD, CD, etc.), a memory (card-type memory, ROM, etc.), or the like. The processor such as the CPU performs various types of processing of the present embodiment based on the program (data) stored on the information storage medium. Specifically, a program for causing a computer (an apparatus including an operation unit, a processing unit, a storage unit, and an output unit) to function as various units (data acquisition unit, selection unit, notification control unit, guidance instruction unit, storage unit, etc.) of the present embodiment (i.e., a program for causing a computer to execute the processing of various units) is stored on the information storage medium.

Figure 2A:
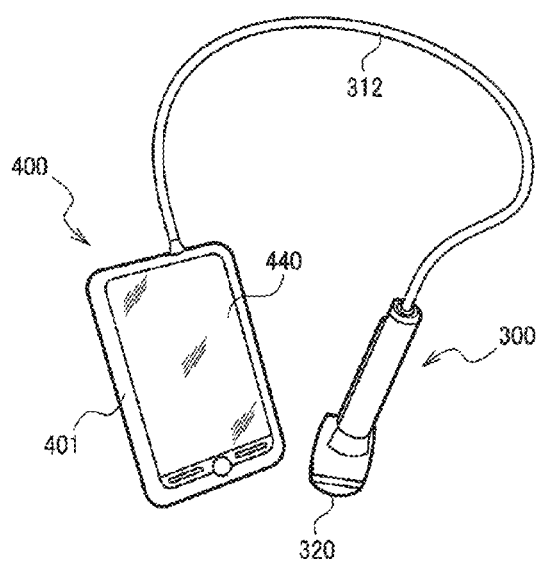
FIGS. 2A to 2C show examples of the specific device configuration of the ultrasonic measuring device.
Figure 2C:
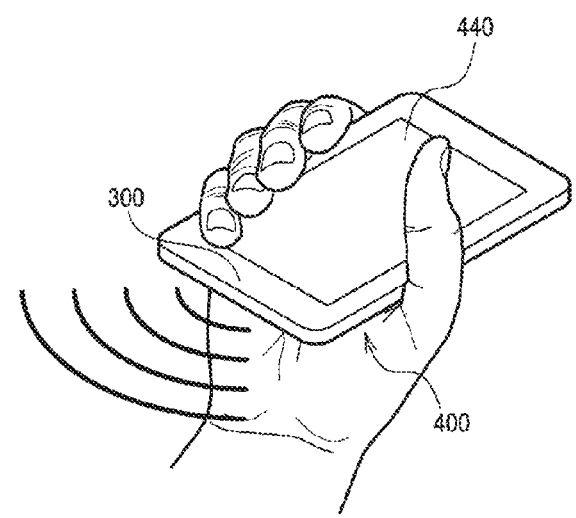
Figure 2B:
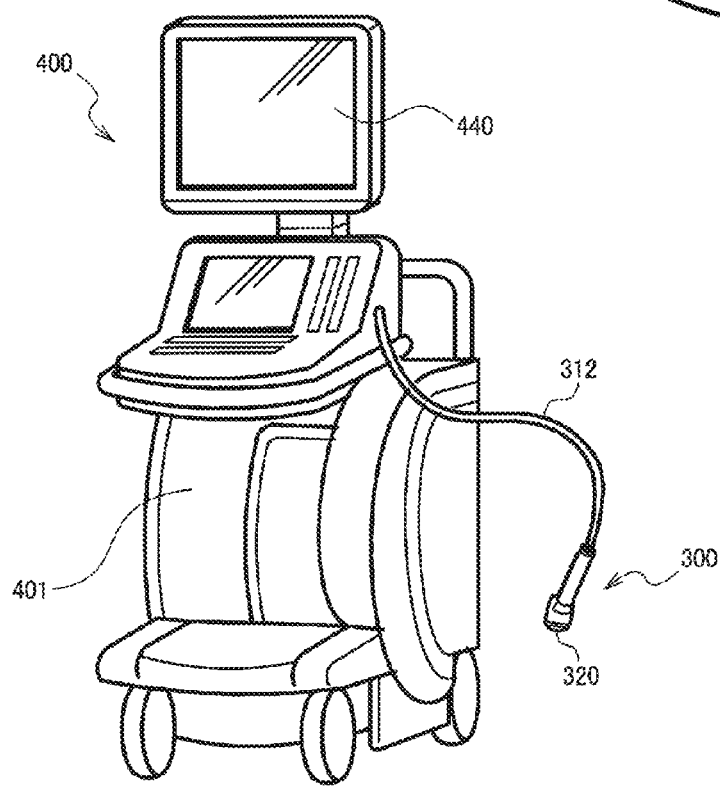

FIGS. 2A to 2C show examples of the specific device configuration of the ultrasonic measuring device (in a broad sense, an electronic device) of the present embodiment. FIG. 2A shows an example of a handheld type of ultrasonic measuring device 400, and FIG. 2B shows an example of a stationary type of ultrasonic measuring device 400. FIG. 2C shows an example of an integrated ultrasonic measuring device 400 in which an ultrasonic probe 300 is built into the body.

The ultrasonic measuring device 400 in FIGS. 2A and 2B includes the ultrasonic probe 300 and an ultrasonic measuring device body 401 (in a broad sense, an electronic device body), and the ultrasonic probe 300 and the ultrasonic measuring device body 401 are connected by a cable 312. A probe head 320 is provided in the tip portion of the ultrasonic probe 300, and a display unit 440 for displaying images is provided on the ultrasonic measuring device body 401. In FIG. 2C, the ultrasonic measuring device 400 has the display unit 440, and the ultrasonic probe 300 is built into the ultrasonic measuring device 400. In the case of FIG. 2C, the ultrasonic measuring device 400 can be realized by a general-purpose mobile information terminal such as a smartphone.

2. Procedure of Present Embodiment

Figure 3A:
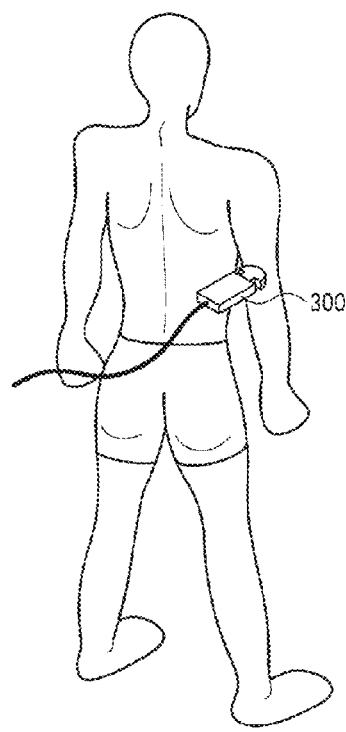
FIGS. 3A to 3D are diagrams illustrating measurement performed using the ultrasonic measuring device.
Figure 3C:
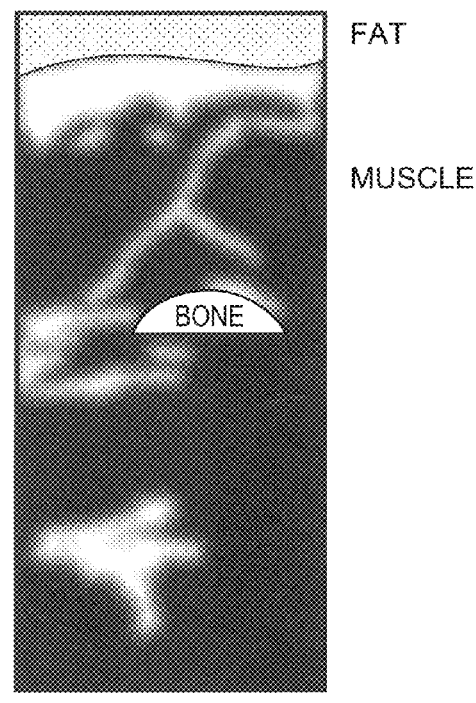
Figure 3B:
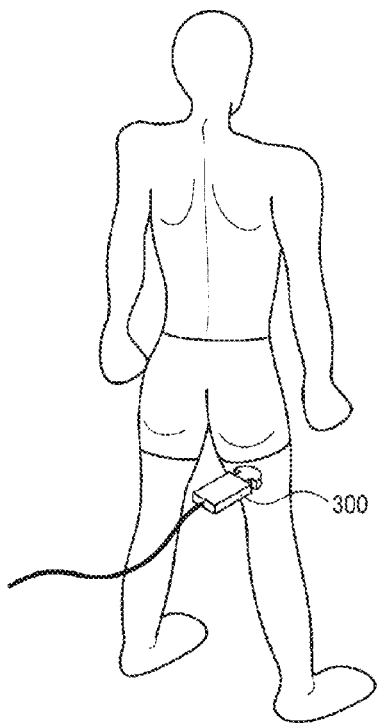
Figure 3D:
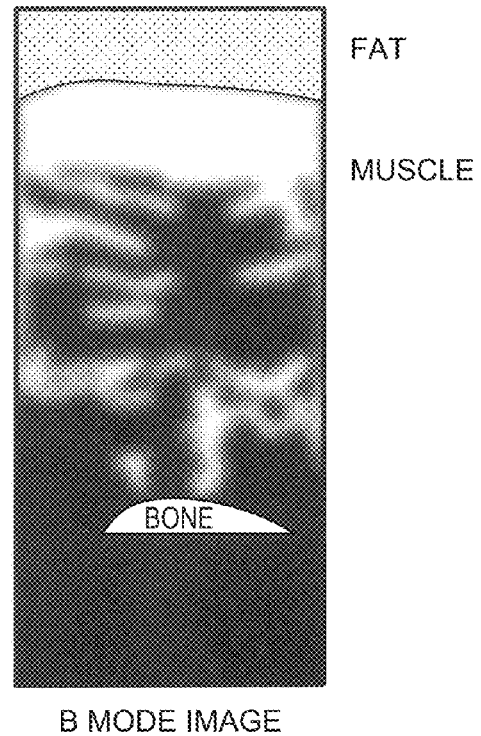

FIGS. 3A and 3B are diagrams showing how the ultrasonic probe 300 is pressed against a measurement location on the user's body, and how the state of fat and muscle is measured. FIG. 3A shows the case where the ultrasonic probe 300 is pressed against the back of the user's arm. In this case, the B-mode image illustrated in FIG. 3C is displayed on the display unit 440. FIG. 3B shows the case where the ultrasonic probe 300 is pressed against the back of the user's thigh. In this case, the B-mode image illustrated in FIG. 3D is displayed on the display unit 440. The luminance is the brightest for the bone portions in these B-mode images. This is because bone has a higher ultrasonic reflectivity than the surrounding body tissue, and also a higher A-mode waveform amplitude.

In the case of performing measurement as shown in FIGS. 3A and 3B, there is the issue that it is difficult for the user to check the orientation of the ultrasonic probe 300 relative to the measurement location while also watching the B-mode image shown in FIGS. 3C and 3D in order to make adjustments to achieve appropriate measurement. In other words, in the case where measurement is performed while pressing the ultrasonic probe 300 against a measurement location on the rear side of the user's body as shown in FIGS. 3A and 3B, it is difficult for the user to check the B-mode image displayed on the display unit 440 of the ultrasonic measuring device while also making adjustments to achieve appropriate measurement. That is to say, when the user performs measurement himself/herself, it is difficult to determine whether the measurement results have been successfully obtained or not while also viewing the B-mode image. In particular, with a handheld type of ultrasonic measuring device as shown in FIGS. 2A and 2C, the distance between the ultrasonic probe 300 and the display unit 440 is small. For this reason, it is difficult for the user to check the B-mode image, which is the measurement result image displayed on the display unit 440, while also pressing the ultrasonic probe 300 against the measurement location.

Figure 4:
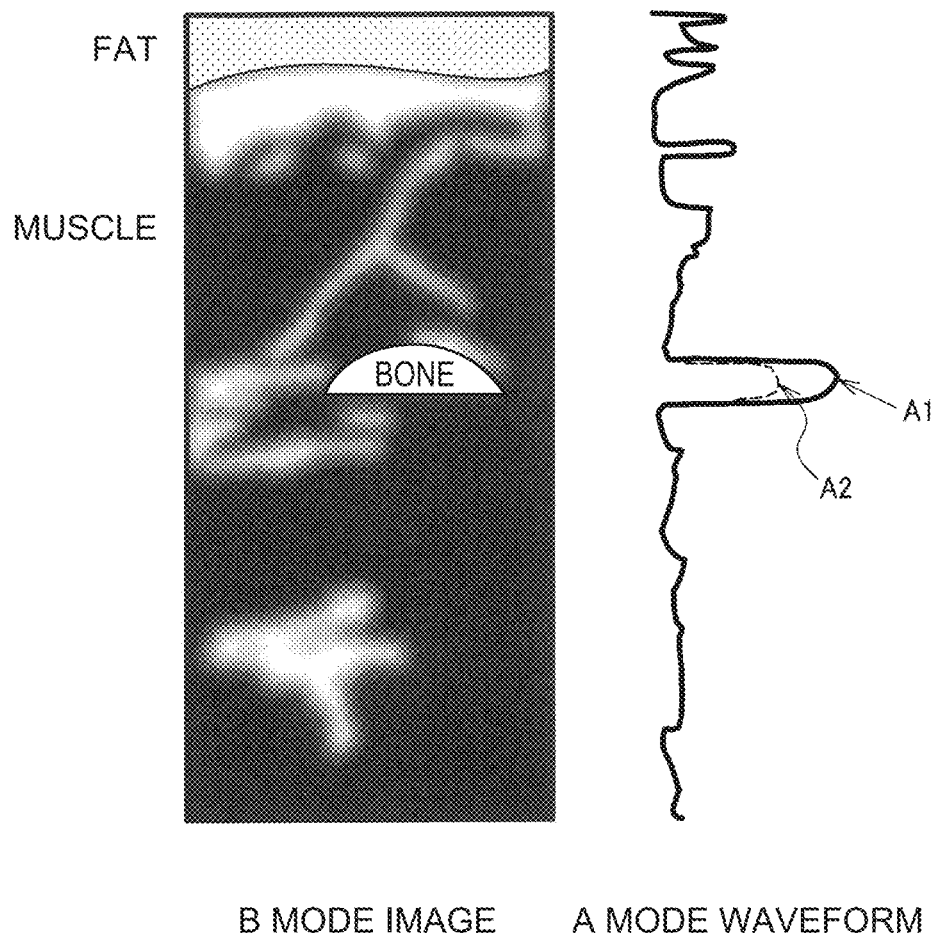
FIG. 4 is a diagram illustrating an A-mode waveform and a B-mode image.

The ultrasonic measuring device has two display methods (measurement methods) called the A-mode and the B-mode. As shown in FIG. 4, in the A-mode, an A-mode waveform that is a rendering of the amplitude of the ultrasonic signal (reception signal) relative to the depth (distance in the depth direction) is displayed. In the B-mode, a B-mode image that is a two-dimensional image obtained by converting the amplitude of the ultrasonic signal into luminance is displayed. For example, body tissue that has a high ultrasonic reflectivity such as bone is rendered in white, which has a high luminance. On the other hand, body tissue that has a low ultrasonic reflectivity is rendered in black, which has a low luminance. This B-mode image can be generated by converting the amplitude in the A-mode waveform data into luminance.

Figure 5:
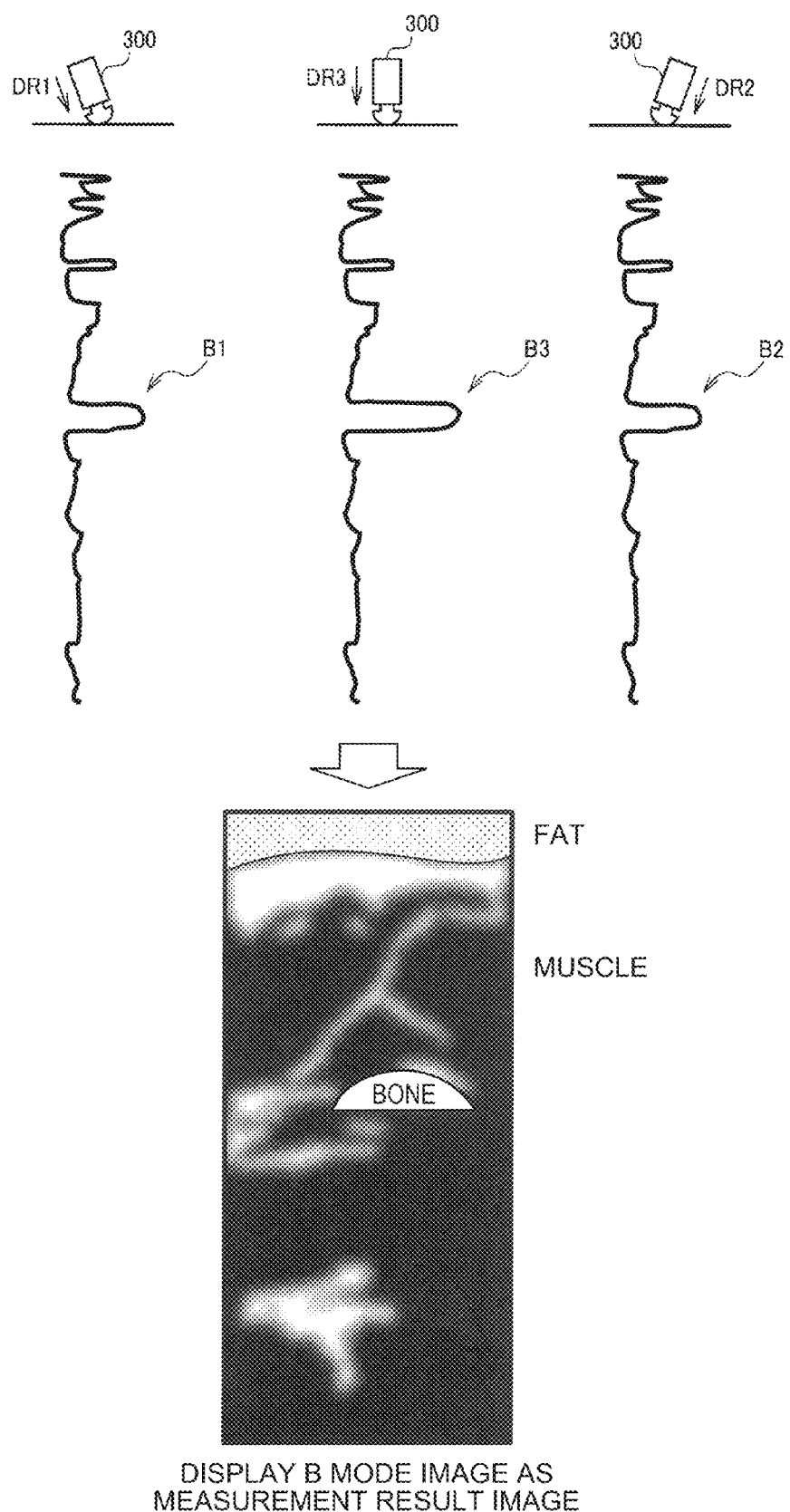
FIG. 5 is a diagram illustrating a procedure according to the embodiment.

In the present embodiment, as shown by A1 and A2 in FIG. 4, the amplitude of the peak waveform that corresponds to specific body tissue such as bone changes according to the direction of the scanning plane of the ultrasonic beam relative to the measurement location surface (body surface) (i.e., the angle formed by the scanning plane and the measurement location surface), and focusing on this fact, the technique shown in FIG. 5 is employed.

For example, the A-mode waveform data pieces acquired at B1, B2, and B3 in FIG. 5 are obtained by changing the direction of the scanning plane of the ultrasonic beam relative to the measurement location surface. For example, the A-mode waveform data pieces acquired at B1, B2, and B3, for example, respectively correspond to the cases where the direction of the scanning plane was first, second, and third directions DR1, DR2, and DR3. Here, the directions DR1 and DR2 are directions that are not perpendicular to the body surface at the measurement location, and are not appropriate scanning plane directions. For this reason, the A-mode waveform data pieces for B1 and B2 have a smaller amplitude at the peak waveform of interest corresponding to bone. Note that the A-mode waveform data pieces for B1, B2, and B3 in FIG. 3 are obtained by performing averaging processing, selection processing, or the like on the A-mode waveform data groups acquired when the scanning plane directions were the directions DR1, DR2, and DR3.

On the other hand, the direction DR3 is a direction that is perpendicular to the body surface at the measurement location, and is an appropriate scanning plane direction. For this reason, in the A-mode waveform data piece for B3, the amplitude at the peak waveform of interest corresponding to bone is higher than the amplitudes in the A-mode waveform data pieces for B1 and B2, and thus is the highest. In other words, when the direction of the scanning plane of the ultrasonic beam is appropriate, the amplitude of the peak waveform of interest is also higher.

In view of this, in the present embodiment, among multiple A-mode waveform data pieces (1st to K-th A-mode waveform data pieces; the same follows hereinafter), the A-mode waveform data piece in which the amplitude of the peak waveform of interest is the highest (greater than or equal to a predetermined threshold value) as shown by B3 is selected as the measurement result A-mode waveform data piece. A measurement result image (in a broad sense, notification data) that is based on the selected measurement result A-mode waveform data piece is displayed on the display unit 440 (in a broad sense, a notification unit). Specifically, in FIG. 5, among the A-mode waveform data pieces for B1, B2, and B3, at which the scanning plane directions are DR1, DR2, and DR3 (in a broad sense, 1st to K-th directions), or in a broad sense, among the 1st to K-th A-mode waveform data pieces obtained from the 1st to K-th A-mode waveform data groups, the A-mode waveform data piece for B3, at which the scanning plane direction is DR3 (in a broad sense, the L-th direction), or in a broad sense, the L-th A-mode waveform data piece is selected as the measurement result A-mode waveform data piece. A B-mode image that is based on the selected A-mode waveform data piece for B3 (a B-mode image generated based on the A-mode waveform data group that corresponds to that A-mode waveform data piece) is then displayed as the measurement result image.

According to this configuration, the A-mode waveform data piece that was acquired when the scanning plane direction was appropriate, that is to say, when the direction of the scanning plane of the ultrasonic beam was perpendicular (substantially perpendicular) to the body surface at the measurement location, is selected, and a corresponding B-mode image is displayed. For example, if the user performs measurement by pressing the ultrasonic probe against his/her own body while changing the direction of the scanning plane of the ultrasonic beam, a B-mode image that corresponds to the appropriate scanning plane direction is automatically generated and displayed on the display unit 440. Accordingly, even if the user cannot view the screen of the display unit 440, a B-mode image that corresponds to the case where the scanning plane direction is an ideal direction as shown by B3 in FIG. 5 is displayed, and it is possible to obtain correct measurement results.

With a handheld type of ultrasonic measuring device as shown in FIGS. 2A and 2C, for example, there is the issue that it is difficult for the user to figure out the appropriate scanning plane direction while viewing the screen of the display unit 440.

With regards to this point, according to the technique of the present embodiment, even if the user does not check the screen of the display unit 440, a B-mode image that corresponds to the appropriate scanning plane direction is automatically generated and displayed as a measurement result image, thus resolving the above-described issue and enabling an improvement in user operability and user-friendliness. Also, according to the present embodiment, it is possible to, for example, switch off the display of the display unit 440 during measurement, and then display only the most appropriate B-mode image that was obtained from the A-mode waveform data piece at B3 in FIG. 5 on the display unit 440 when measurement ends. In other words, instead of successively displaying B-mode images that are successively obtained in the measurement period, only the B-mode image having the highest amplitude at the peak waveform of interest is displayed. This enables shortening the time period for which the display of the display unit 440 is switched on so as to achieve low power consumption for the ultrasonic measuring device, for example, and enables realizing power conservation particularly in the case of a handheld type of ultrasonic device.

Note that it is desirable that the peak waveform of interest to be subjected to the amplitude magnitude comparison processing is set in accordance with the corresponding measurement location. For example, since the depth of bone from the body surface changes depending on the measurement location as shown in FIGS. 3C and 3D, the peak waveform of interest depth range is also set differently for each measurement location. Also, when the user inputs the measurement location, the depth range setting that corresponds to the input measurement location is read out, and peak waveform of interest amplitude comparison processing is performed in accordance with that depth range as shown by B1, B2, and B3 in FIG. 5. According to this configuration, it is possible to select appropriate peak waveforms of interest at various measurement locations, compare the magnitudes of the amplitudes, and display a B-mode image that corresponds to the appropriate scanning plane direction.

Also, although the case of applying the technique of the present embodiment to the measurement of fat thickness and muscle thickness in a human body has been described above, the present embodiment is not limited to this case. For example, the technique of the present embodiment may be applied to the examination of meat quality and the examination of animal products such as beef cattle and pork products at the time of shipment. For example, the technique of the present embodiment may be applied to the detection of the rib-eye position in order to determine the meat quality (marbling) of beef cattle.

Figure 6A:
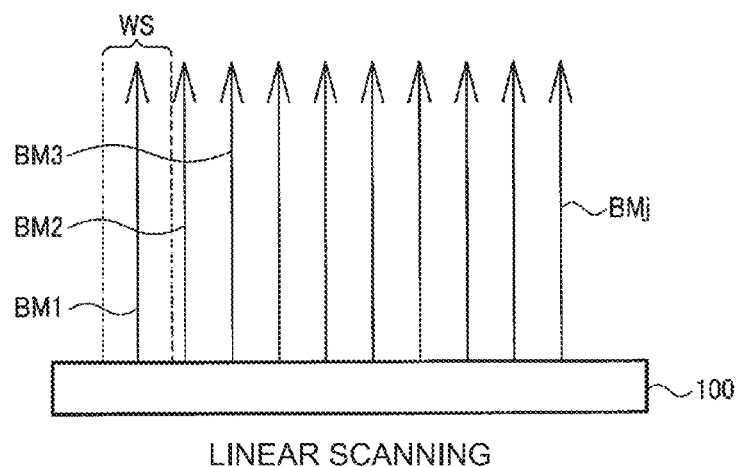
FIGS. 6A to 6C are diagrams illustrating a linear scanning system and a sector scanning system.

The B-mode image in FIG. 5 is an example of an image generated with the linear scanning system shown in FIG. 6A. Note that the technique for generating and acquiring the B-mode image and the A-mode waveform data pieces is not limited to this, and the sector scanning method shown in FIG. 6B may be used.

In one example, with the linear scanning system shown in FIG. 6A, A-mode waveform data pieces are acquired while shifting between ultrasonic emission/reception signal channels one at a time, and the amplitudes of the A-mode waveform data groups acquired by one instance of linear scanning, for example, are converted into luminance so as to generate a B-mode image. In this case, the A-mode waveform data pieces that are to be subjected to the selection processing described using B1 to B3 in FIG. 5 can be obtained by performing averaging processing on the A-mode waveform data groups acquired by one instance of linear scanning, for example. In other words, the A-mode waveform data pieces for B1 to B3 that are to be subjected to selection processing are obtained by performing averaging processing on the amplitudes at each depth in the A-mode waveform data pieces in each A-mode waveform data group. Alternatively, a configuration is possible in which representative A-mode waveform data pieces (e.g., A-mode waveform data pieces in the vicinity of the center in linear scanning) are selected from among the A-mode waveform data groups acquired by one instance of linear scanning, and those representative A-mode waveform data pieces are used as the A-mode waveform data pieces for B1 to B3 that are to be subjected to selection processing.

Figure 7:
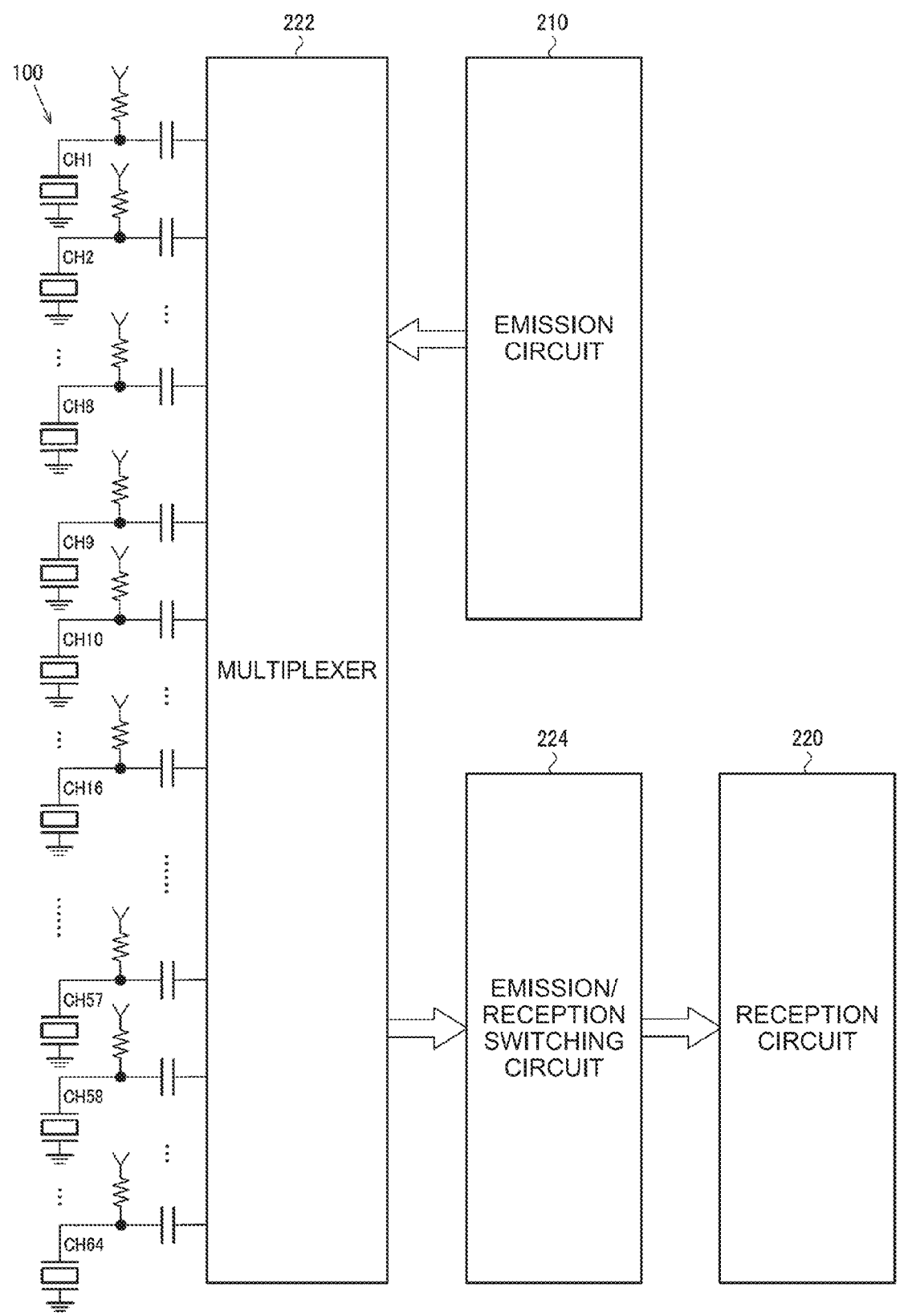
FIG. 7 is a diagram illustrating the linear scanning system and the sector scanning system in detail.

FIG. 7 is a diagram illustrating the linear scanning system and the sector scanning system in detail. In the linear scanning system, the multiplexer 222 operates so as to successively select linear scan target channels from among channels CH1 to CH64 of the ultrasonic transducer device 100.

For example, first, the channels CH1 to CH8 are selected as linear scan targets, and an emission signal (emission pulse) is output from the emission circuit 210 to the channels CH1 to CH8 of the ultrasonic transducer device 100 via the multiplexer 222. Accordingly, an ultrasonic beam BM1 shown in FIG. 6A is emitted (radiated, generated), for example. Then, reception signals from the channels CH1 to CH8 are input to the reception circuit 220 via the multiplexer 222 and the emission/reception switching circuit 224.

Next, the channels CH2 to CH9 are selected as the linear scan targets, and an emission signal is output from the emission circuit 210 to the channels CH2 to CH9. Accordingly, an ultrasonic beam BM2 shown in FIG. 6A is emitted, for example. Reception signals from the channels CH2 to CH9 are then input to the reception circuit 220. Channels for linear scanning are successively selected in this way, then lastly the channels CH57 to CH64 are selected, and an ultrasonic beam BMj shown in FIG. 6A is emitted, for example. Thus, one instance of scanning (linear scanning) ends, and the second instance of scanning is performed next.

The A-mode waveform data groups of the present embodiment are each a group made up of multiple A-mode waveform data pieces acquired by one instance of scanning in this way, for example. Performing averaging processing or selection processing on these A-mode waveform data pieces obtains the A-mode waveform data pieces (1st to K-th A-mode waveform data pieces) for the respective A-mode waveform data groups (1st to K-th A-mode waveform data groups).

On the other hand, in the sector scanning system, all of the channels CH1 to CH64 are selected, for example. An emission signal is then output from the emission circuit 210 to all of the channels CH1 to CH64 of the ultrasonic transducer device 100. Accordingly, ultrasonic beams BM1 to BMj shown in FIG. 6B are emitted.

Figure 6B:
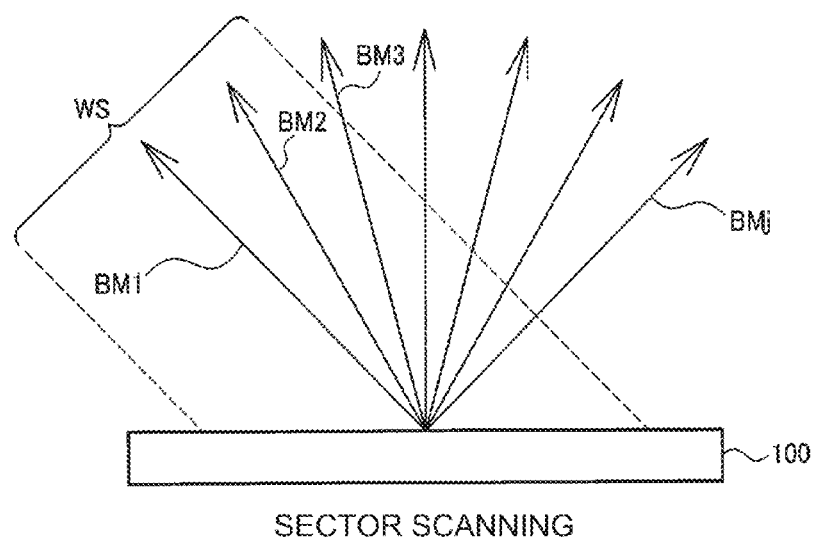

In this case, with the sector scanning system, the ultrasonic beams BM1 to BMj are emitted in various directions as shown in FIG. 6B by performing control for delaying the emission start timing of the emission signal from the emission circuit 210. For example, the emission of the ultrasonic beam BM1 shown in FIG. 6B is realized by delaying the emission start timing of the ultrasonic transducer element on the left side of the sheet, and making the emission start timing of the ultrasonic transducer element on the right side earlier. On the other hand, the emission of the ultrasonic beam BMj is realized by making the emission start timing of the ultrasonic transducer element on the left side of the sheet earlier, and delaying the emission start timing of the ultrasonic transducer element on the right side.

In FIGS. 6A and 6B, the scanning plane of the ultrasonic transducer device 100 is the plane that the ultrasonic beams BM1 to BMj emitted in the scans conform to, and is a plane that is parallel to the paper plane in FIGS. 6A and 6B.

Figure 6C:
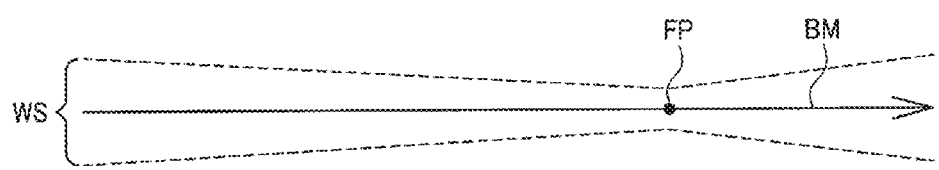

Note that with the linear scanning in FIG. 6A, the ultrasonic beams emitted from the ultrasonic transducer device 100 have an emission width WS that corresponds to the width of the selected channels (e.g., the channels CH1 to CH8). Also, with the sector scanning in FIG. 6B, the ultrasonic beams emitted from the ultrasonic transducer device 100 have an emission width WS that spans the entire width of the linear device (or the width of the sector scan target channels). As shown in FIG. 6C, ultrasonic beam emission focus control is performed using emission signal delay control, an acoustic lens, or the like such that the width in the scanning direction converges on a focal point FR.

Also, although the case where the measurement result image (notification data) is the B-mode image is shown as an example in FIG. 5, the measurement result image of the present embodiment is not limited in this way, and it may be an image including numbers, characters, symbols, or the like that express the ultrasonic measurement results, for example. For example, an image including numbers or the like that express the ultrasonic measurement results obtained when the scanning plane direction was DR3 (L-th direction) in FIG. 5 may be displayed as the measurement result image on the display unit 440. FIG. 8 shows an example of such an image including numbers that express the measurement result. Numbers indicating the fat thickness and the muscle thickness that were obtained by performing ultrasonic measurement at a site on the back of the arm are displayed in the measurement result image in FIG. 8, along with numbers indicating reference values for the fat thickness and the muscle thickness. These measurement results can be obtained by performing analytical processing on the selected A-mode waveform data piece at B3 in FIG. 5, for example. Also, the notification data of the present embodiment may be audio expressing the measurement result, or the like. For example, the measurement results shown in FIG. 8 may be read aloud.

Figure 9:
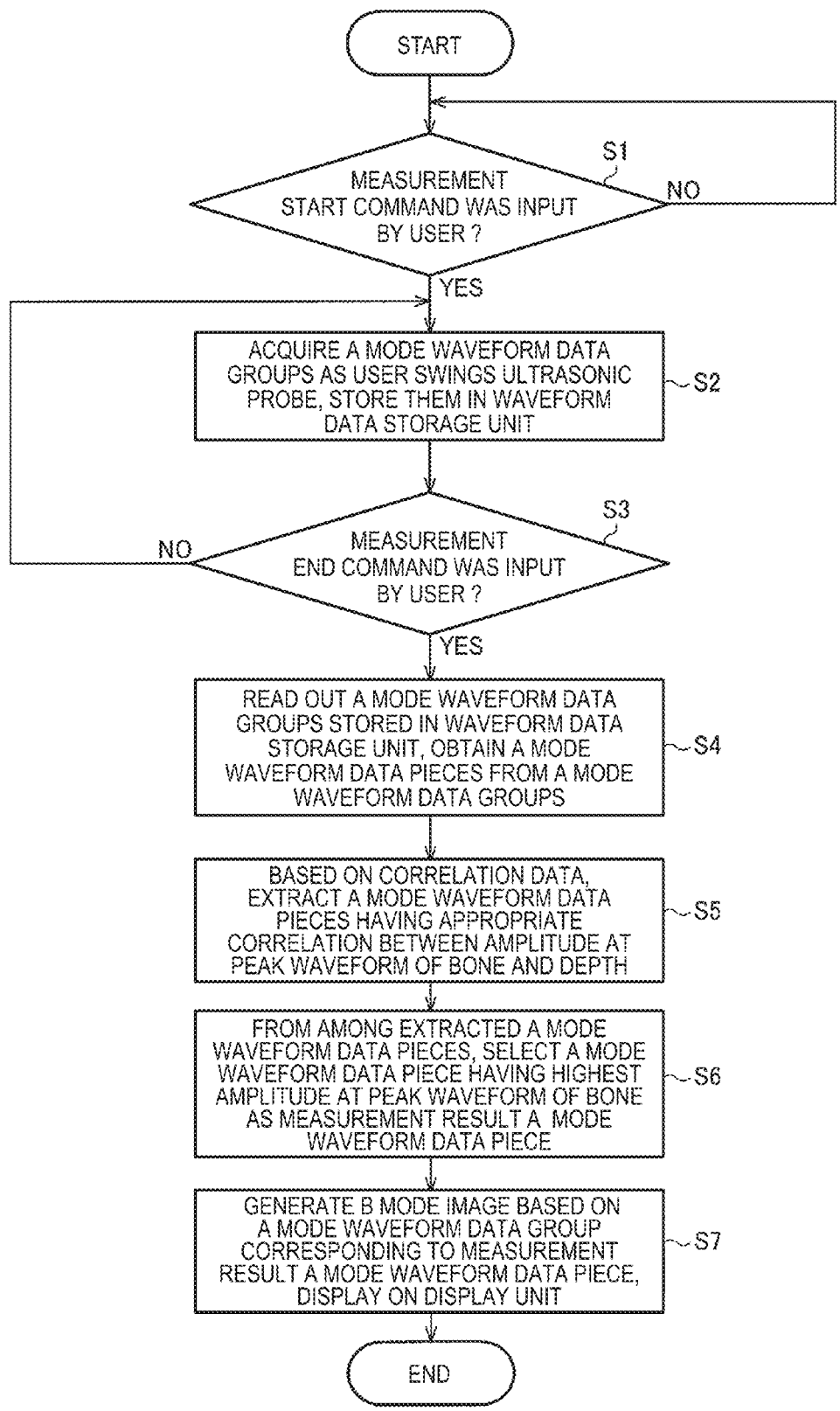
FIG. 9 is a flowchart showing detailed processing in the procedure according to the embodiment.

FIG. 9 is a flowchart showing details of processing performed in the present embodiment. First, it is determined whether or not an ultrasonic measurement start command was input by the user (step S1). Then, in the measurement period, which is the period from when the measurement start command is input by the user until when a measurement end command is input, A-mode waveform data groups are acquired and stored in the waveform data storage unit 252 shown in FIG. 1 (steps S2 and S3). In other words, the user swings the ultrasonic probe while pressing it against the measurement location in the measurement period. For example, the user swings the ultrasonic probe, with the line arrangement direction (scanning direction) of the linear element array in the head of the ultrasonic probe serving as the center of rotation. A-mode waveform data groups are then acquired for the various scanning plane directions as described using FIG. 5, and saved in the waveform data storage unit 252. Note that the user can input the measurement start command and the measurement end command by operating operation buttons or a touch panel of the ultrasonic measuring device in FIGS. 2A to 2C.

When the measurement period ends, the A-mode waveform data groups stored in the waveform data storage unit 252 are read out, and A-mode waveform data pieces are obtained from the A-mode waveform data groups through the above-described averaging processing or selection processing (step S4). Then, based on later-described correlation data, the A-mode waveform data pieces for which it is determined that the correlation between the amplitude at the peak waveform of bone and the depth is appropriate are extracted (step S5).

Next, from among the extracted A-mode waveform data pieces, the A-mode waveform data piece having the highest amplitude at the peak waveform of bone as shown by B3 in FIG. 5 is selected as the measurement result A-mode waveform data piece (step S6). Note that the unselected and unused A-mode waveform data pieces (and the corresponding A-mode waveform data groups) are deleted, for example. A B-mode image is then generated based on the A-mode waveform data group that corresponds to the selected measurement result A-mode waveform data piece, and is displayed on the display unit 440 (step S7). For example, as shown by B3 in FIG. 5, a B-mode image is generated based on the A-mode waveform data group that was acquired by linear scanning when the ultrasonic scanning plane direction was perpendicular to the body surface, and that B-mode image is displayed on the display unit 440. According to this configuration, due to the user merely swinging the ultrasonic probe while pressing it against the measurement location, a B-mode image obtained by linear scanning at an appropriate scanning plane direction is automatically generated and displayed on the display unit 440.

Figure 10:
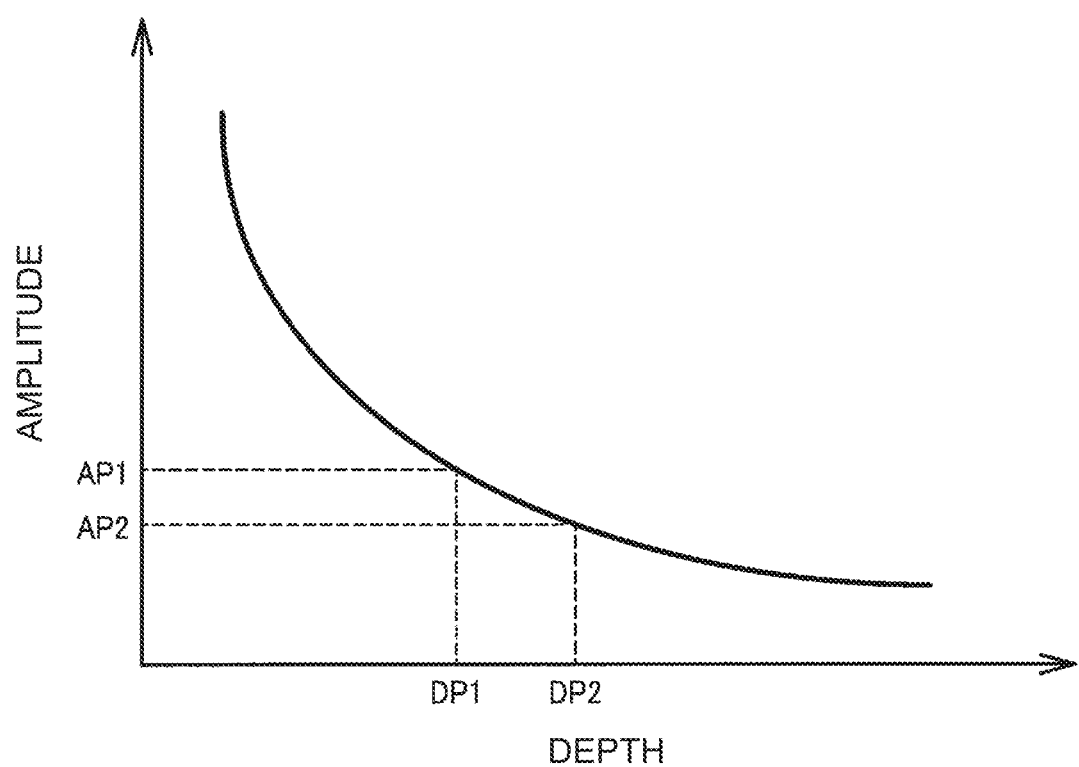
FIG. 10 is a diagram illustrating correlation data representing the correlation between amplitude in an A-mode waveform and depth.

FIG. 10 is a schematic diagram illustrating correlation data used in step S5 of FIG. 9. For example, the amplitude of the A-mode waveform (the amplitude of the ultrasonic reception signal) attenuates according to the depth from the body surface. In view of this, correlation data representing the correlation between the amplitude of the A-mode waveform and depth as shown in FIG. 10 is stored in the correlation data storage unit 254 shown in FIG. 1. For example, correlation data representing the correlation between the amplitude of the A-mode waveform and depth is stored in association with various measurement locations, such as the back of the arm and the back of the leg.

Then, the A-mode waveform data piece for which it was determined that the correlation between the amplitude at the peak waveform of interest and the depth is appropriate based on the correlation data is selected as the measurement result A-mode waveform data piece. For example, the A-mode waveform data pieces that are to be subjected to selection processing in FIG. 5 are extracted based on the correlation data, and a measurement result A-mode waveform data piece is selected from among the extracted A-mode waveform data pieces.

For example, in the case where the peak waveform of interest (bone) at the corresponding measurement location is in the depth range of DP1 to DP2, it can be determined, based on the correlation data in FIG. 10, that the amplitude of that peak waveform of interest is in the amplitude range of AP1 to AP2. In view of this, only A-mode waveform data pieces for which the amplitude of the peak waveform of interest is in the amplitude range of AP1 to AP2 are extracted as the waveform data pieces that are to be subjected to selection processing in FIG. 5. According to this configuration, A-mode waveform data pieces that were obtained when, for example, the ultrasonic probe was pointed in a direction very different from the envisioned direction can be excluded from the targets of selection processing in FIG. 5, thus improving the efficiency of processing and the like.

Note that the processing of the present embodiment is not limited to the processing shown in FIG. 9, and can be modified in various ways. For example, the following describes processing according to one variation.

In the processing of this variation, first, one instance of linear scanning is performed, and the multiple (e.g., 57) A-mode waveform data pieces acquired by the linear scanning are stored as the first A-mode waveform data group. Averaging processing is then performed on the acquired A-mode waveform data pieces in order to generate the first A-mode waveform data piece.

At the next predetermined timing, the second instance of linear scanning is performed, multiple A-mode waveform data pieces are acquired at a scanning plane direction (second direction) that is different from the scanning plane direction in the first instance (first direction), for example, and these acquired A-mode waveform data pieces are stored as the second A-mode waveform data group. Averaging processing is then performed on the acquired A-mode waveform data pieces in order to generate the second A-mode waveform data piece.

Then, the highest amplitude value in the first A-mode waveform data piece and the highest amplitude value in the second A-mode waveform data piece are compared. The A-mode waveform data piece whose highest amplitude value is higher is selected as the provisional measurement result A-mode waveform data piece and saved, and the A-mode waveform data piece with the smaller value and the corresponding A-mode waveform data group are discarded.

At the next predetermined timing, the third instance of linear scanning is performed, multiple A-mode waveform data pieces are acquired at a scanning plane direction (third direction) that is different from the scanning plane direction in the second instance, for example, and these acquired A-mode waveform data pieces are stored as the third A-mode waveform data group. Averaging processing is then performed on the acquired A-mode waveform data pieces in order to generate the third A-mode waveform data piece.

Then, the highest amplitude value in the third A-mode waveform data piece and the highest amplitude value in the measurement result A-mode waveform data piece that was previously selected and saved are compared. The A-mode waveform data piece whose highest amplitude value is higher is selected as the updated measurement result A-mode waveform data piece and saved, and the A-mode waveform data piece with the smaller value and the corresponding A-mode waveform data group are discarded.

The above processing is repeated a predetermined number of times (K times). Then, at the end of the K-th instance of linear scanning and the selection and saving of the measurement result A-mode waveform data piece based on the K-th A-mode waveform data piece, notification data is generated based on at least one of the measurement result A-mode waveform data piece and the measurement result A-mode waveform data group that corresponds to the measurement result A-mode waveform data piece. The notification unit 439 then performs notification of the generated notification data. For example, a B-mode image is generated based on the measurement result A-mode waveform data group and displayed on the display unit 440. Alternatively, characters, numbers, and the like expressing the measurement results as shown in FIG. 8 are displayed, or the measurement results are read aloud.

According to the processing of this variation, unnecessary A-mode waveform data pieces and corresponding A-mode waveform data groups are successively discarded, thus making it possible to reduce the amount of storage used in the storage unit 250. Note that although the case of applying the technique of the present embodiment to the linear scanning shown in FIG. 6A has mainly been described as an example above, the technique of the present embodiment is also applicable to the sector scanning shown in FIG. 6B, for example.

3. Reference A-Mode Waveform Data

In one conceivable example of an application of the ultrasonic measuring device, workout effectiveness or the like is checked by measuring fat thickness and muscle thickness after a workout. Checking workout effectiveness requires reference data for comparison with measured data.

In view of this, in the present embodiment, reference A-mode waveform data for a test subject, such as the user who is to be subjected to ultrasonic measurement, is stored in the reference data storage unit 256 shown in FIG. 1. Then, a measurement result A-mode waveform data piece is selected by performing comparison processing in which A-mode waveform data pieces obtained from A-mode waveform data groups acquired by ultrasonic measurement are compared with the reference A-mode waveform data stored in the reference data storage unit 256.

Figure 11:
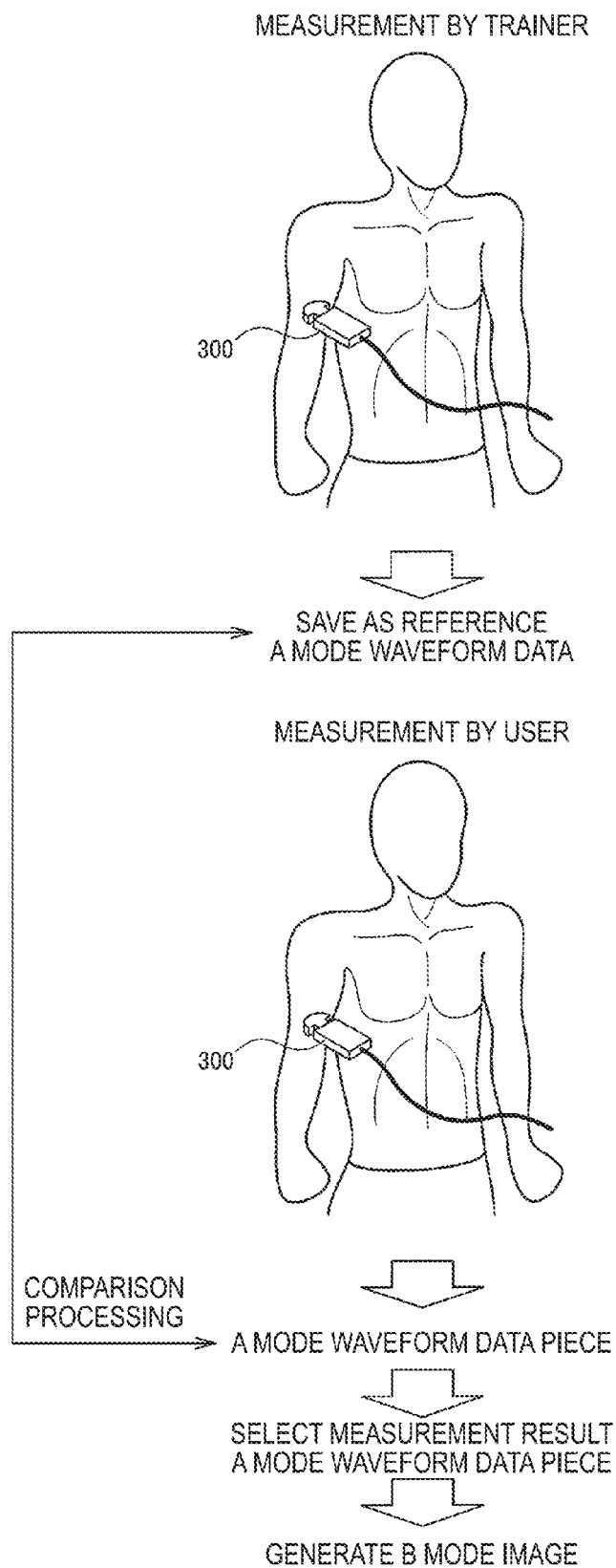
FIG. 11 is a diagram illustrating a procedure according to the embodiment that employs reference A-mode waveform data.

As shown in FIG. 11 for example, first, when measurement is performed for the first time, the trainer who is instructing the user presses the ultrasonic probe 300 against a measurement location on the user's body and performs ultrasonic measurement to obtain a fat thickness and a muscle thickness, and those measurement results are saved as reference A-mode waveform data. Specifically, the measured reference A-mode waveform data is saved in the reference data storage unit 256 as the user's personal data. Since measurement is performed by a highly-skilled trainer, more accurate and appropriate A-mode waveform data is recorded as reference A-mode waveform data for that user.

Figure 12:
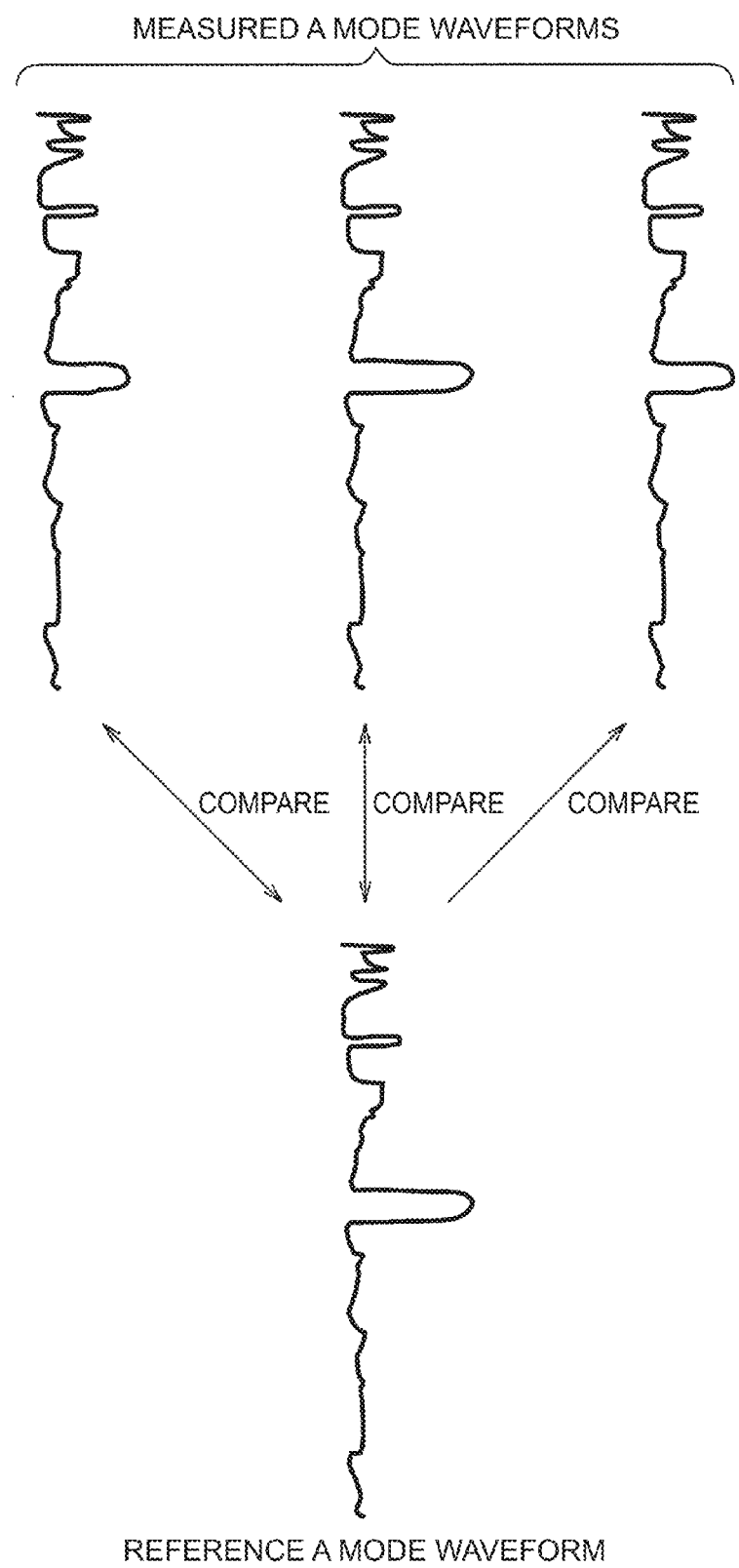
FIG. 12 is another diagram illustrating the procedure according to the embodiment that employs reference A-mode waveform data.

Next, after the workout finishes, for example, the user then presses the ultrasonic probe 300 against the measurement location and performs measurement. As shown in FIG. 12, comparison processing is then performed to compare the multiple A-mode waveform data pieces acquired by the measurement performed by the user with the saved reference A-mode waveform data that was measured by the trainer. Due to this comparison processing, a measurement result A-mode waveform data piece is selected from among the A-mode waveform data pieces measured by the user, and a B-mode image that corresponds to the selected measurement result A-mode waveform data piece is generated. Note that the A-mode waveform data pieces shown in FIG. 12 correspond to the 1st to K-th A-mode waveform data pieces that are obtained by performing averaging processing or selection processing on the 1st to K-th A-mode waveform data groups acquired by performing scanning K times as described above, for example.

Specifically, in the above-described comparison processing, the amplitude of the peak waveform of interest of each of the A-mode waveform data pieces (1st to K-th A-mode waveform data pieces) measured by the user is compared with the amplitude of the peak waveform of interest of the saved reference A-mode waveform data. Then, among the multiple A-mode waveform data pieces, the A-mode waveform data piece in which the amplitude at the peak waveform of interest is closest to the amplitude at the peak waveform of interest in the reference A-mode waveform data is selected as the measurement result A-mode waveform data piece, and a B-mode image is generated.

As described above, when the user performs measurement himself/herself, there is the issue that it is difficult for the user to determine whether the measurement results have been successfully obtained or not while also viewing the B-mode image.

In view of this, in the present embodiment, appropriate and ideal reference A-mode waveform data is measured in advance and recorded. Then, when the user performs measurement while swinging the ultrasonic probe so as to change the scanning plane, the A-mode waveform data piece whose waveform closely resembles that in the recorded reference A-mode waveform data is selected as the measurement result A-mode waveform data piece from among the measured A-mode waveform data pieces. For example, the A-mode waveform data piece in which the amplitude at the peak waveform of bone is close to that in the reference A-mode waveform data is selected. A B-mode image that corresponds to the selected measurement result A-mode waveform data piece is then displayed to the user after measurement ends, thus making it possible for the user to check the measurement results. In other words, due to the user merely performing measurement by swinging the ultrasonic probe while pressing it against the measurement location, an A-mode waveform data piece obtained when the scanning plane direction was appropriate, such as with the reference A-mode waveform data, is automatically selected, and a corresponding B-mode image is displayed to the user after the measurement.

For example, in the case where the reference A-mode waveform data is measured by an experienced trainer, the A-mode waveform data piece that corresponds to the case where the ultrasonic probe was pressed against the measurement location in a manner similar to that when the trainer performed measurement is automatically selected as the measurement result A-mode waveform data piece from among the A-mode waveform data pieces obtained by the measurement performed by the user. Accordingly, even if the user does not take very much care in pressing the ultrasonic probe against his/her body, the A-mode waveform data piece that corresponds to the case where the ultrasonic probe was pressed against his/her body in an ideal manner when the user performed measurement is automatically selected and displayed as a B-mode image, thus enabling a marked improvement in user operability and user-friendliness.

Note that in the present embodiment, the user who is the test subject may be provided with guidance instruction regarding the direction of the scanning plane of the ultrasonic beam. This guidance instruction processing is performed by the guidance instruction unit 238 shown in FIG. 1.

Figure 13A:
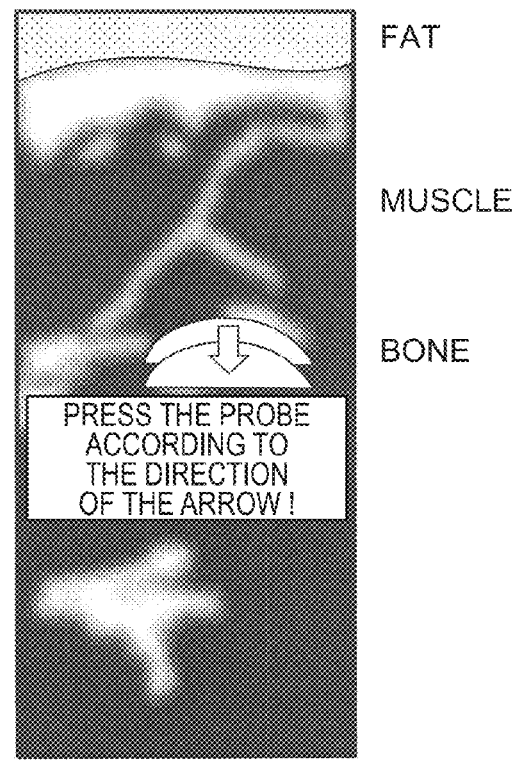
FIGS. 13A and 13B are diagrams illustrating guidance instruction processing.

FIG. 13A shows an example of an image generated in this guidance instruction processing. For example, if the position of the bone (peak waveform of interest) when measurement is performed by the user deviates from the position of the bone when measurement was performed by the trainer, the user is given guidance instruction for changing how the ultrasonic probe is pressed such that the positions match. Specifically, comparison processing is performed for comparing the position (depth) of the peak waveform of interest in the reference A-mode waveform data acquired when measurement was performed by the trainer with the position (depth) of the peak waveform of interest in the A-mode waveform data pieces acquired when measurement is performed by the user, and guidance instruction such as that shown in FIG. 13A is performed based on the results of the comparison processing. According to this configuration, the user can press the ultrasonic probe against the measurement location in a manner similar to that when measurement was performed by the trainer, and it is possible to improve user operability and user-friendliness.

Figure 13B:
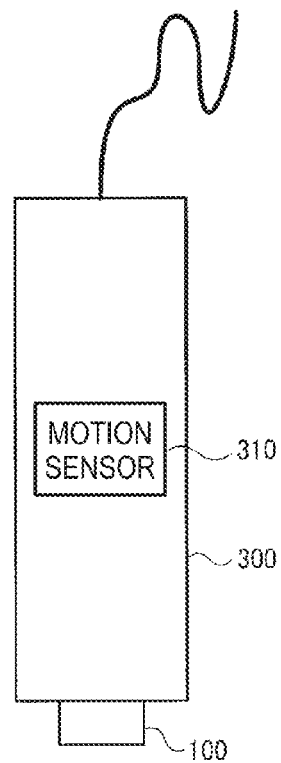

Also, a configuration is possible in which, as shown in FIG. 13B, the ultrasonic probe 300 (ultrasonic measuring device) is internally provided with a motion sensor 310 for detecting user motion (movement), and guidance instruction processing regarding the scanning plane direction is performed based on a motion detection signal from the motion sensor 310. An acceleration sensor (e.g., a 6-axis acceleration sensor) or the like can be envisioned as the motion sensor 310.

According to the technique in FIG. 13B, information indicating the direction and position of the ultrasonic probe 300 when measurement is performed by the trainer can be recorded based on the motion detection signal from the motion sensor 310. When measurement is performed by the user as well, information indicating the direction and position of the ultrasonic probe 300 is obtained based on the motion detection signal from the motion sensor 310, and comparison processing is performed for comparing the obtained direction and position information with the direction and position information obtained when measurement was performed by the trainer. The user is then given guidance instruction based on the results of the comparison processing such that the direction and position match the direction and position when measurement was performed by the trainer. This makes it possible to, for example, store measurement data that was obtained when always performing pressing in the same manner at the same measurement location, and makes it possible for the user to find out small changes in fat thickness, muscle thickness, and the like.

Note that although the case of giving guidance instruction using an image is shown as example in FIG. 13A, the present embodiment is not limited to this case. For example, guidance instruction may be given using audio, or guidance instruction may be given using an indicator such as an LED. In one example, audio or the like is used to inform the user of the direction in which and position at which the ultrasonic probe is to be pressed. According to this configuration, the user can confirm the appropriate manner of pressing the ultrasonic probe using audio or like instead of checking images displayed on the display unit 440, thus improving user-friendliness and the like.

Figure 14:
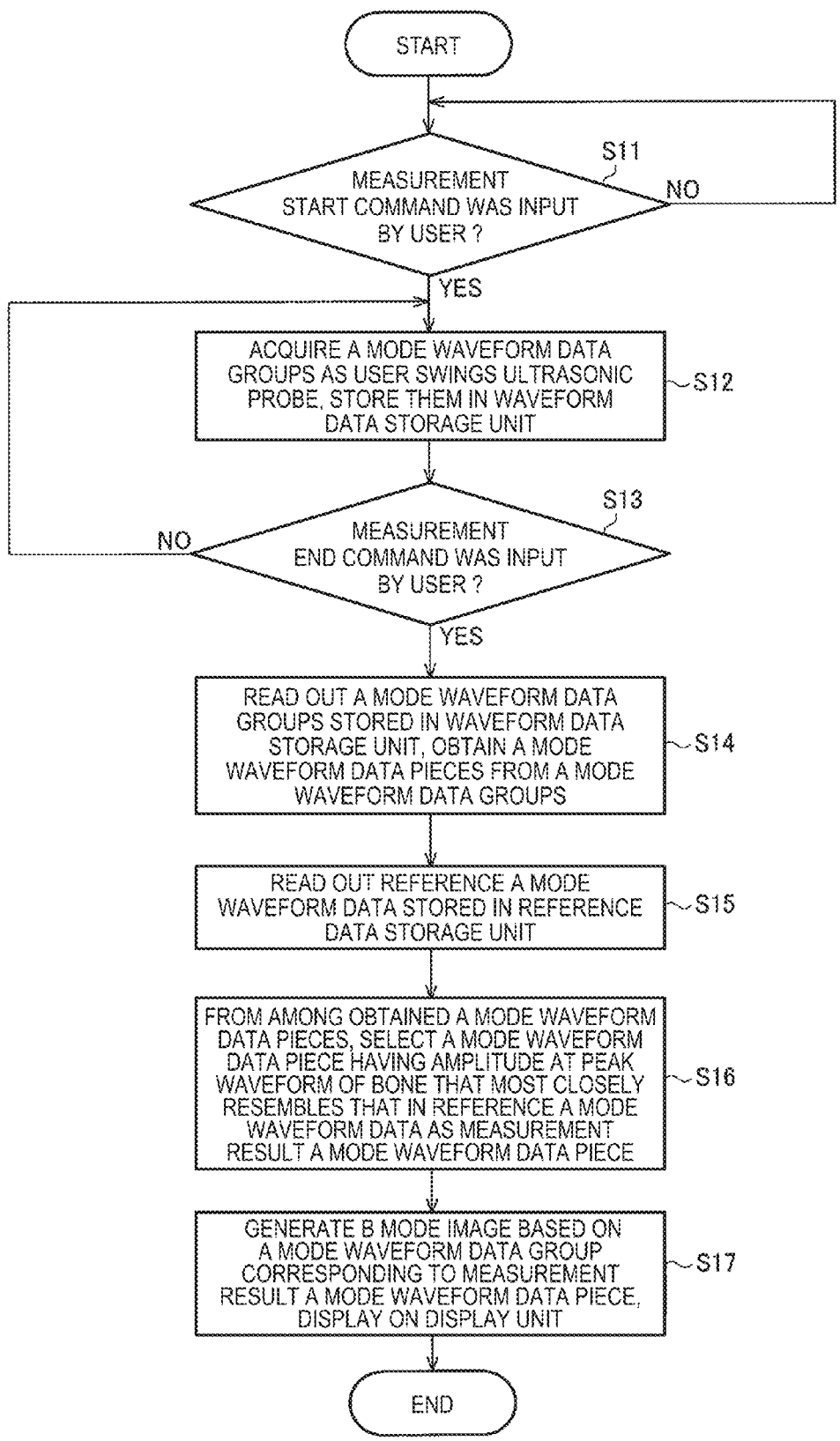
FIG. 14 is a flowchart showing detailed processing of a procedure of the embodiment that employs reference A-mode waveform data.

FIG. 14 is a flowchart showing details of the processing of the present embodiment that was described using FIG. 12. First, it is assumed that in the initial instance of measurement, measurement is performed by the trainer with an appropriate manner of pressing the ultrasonic probe, and the obtained measurement results are stored in the reference data storage unit 256 as reference A-mode waveform data, which is the user's personal data.

When the user subsequently performs measurement, the processing of steps S11 to S13 is performed. The processing of steps S11 to S13 will not be described since it is similar to steps S1 to S3 in FIG. 9.

When the measurement end command is input and the measurement period ends, the A-mode waveform data groups stored in the waveform data storage unit 252 are read out, and A-mode waveform data pieces are obtained from the A-mode waveform data groups through averaging processing or the like (step S14). Also, the reference A-mode waveform data stored in the reference data storage unit 256 is read out (step S15). Then, from among the obtained A-mode waveform data pieces, the A-mode waveform data piece in which the amplitude at the peak waveform of bone is closest to that in the reference A-mode waveform data is selected as the measurement result A-mode waveform data piece (step S16). Note that the unselected and unused A-mode waveform data pieces and the corresponding A-mode waveform data groups are deleted. A B-mode image is then generated based on the A-mode waveform data group that corresponds to the selected measurement result A-mode waveform data piece, and is displayed on the display unit 440 (step S17). According to this configuration, due to the user merely swinging the ultrasonic probe while pressing it against the measurement location, a B-mode image obtained by linear scanning at an appropriate scanning plane direction that is similar to the direction when the trainer performed measurement is automatically generated and displayed on the display unit 440.

Note that although the case where the user swings the ultrasonic probe in step S2 in FIG. 9 and step S12 in FIG. 14 in order to change the direction of the scanning plane of the ultrasonic beam in the measurement period is described above, the present embodiment is not limited to this case. For example, the direction of the ultrasonic scanning plane may be changed by mechanical scanning as shown in FIG. 15.

For example, in FIG. 15, the direction control unit 240 included in the control unit 230 performs direction control for changing the direction of the scanning plane of the ultrasonic beam. The data acquisition unit 232 then acquires the multiple A-mode waveform data groups that are obtained as the direction of the scanning plane of the ultrasonic beam is changed due to the direction control performed by the direction control unit 240. The selection unit 234 then selects a measurement result A-mode waveform data piece based on the A-mode waveform data groups acquired as scanning plane direction control is performed.

Specifically, the direction control unit 240 outputs a drive control signal for controlling the scanning plane direction to a drive unit 110 constituted by a drive mechanism such as a motor. Upon receiving the drive control signal, the drive unit 110 performs driving for changing the direction of the scanning plane of the ultrasonic transducer device 100. Specifically, the direction of the scanning plane of the ultrasonic beam emitted by the ultrasonic transducer device 100 is controlled by mechanical scanning. This enables acquiring A-mode waveform data groups for various scanning plane directions in the measurement period. The technique described in FIG. 5, FIG. 12, or the like is then used to select a measurement result A-mode waveform data piece based on the A-mode waveform data groups acquired in this way, and a corresponding B-mode image is generated. According to this configuration, the ultrasonic beam is automatically emitted with various scanning plane directions in the measurement period without the user swinging the ultrasonic probe, and an appropriate measurement result A-mode waveform data piece is automatically selected based on the A-mode waveform data groups acquired in this way. This enables reducing the operational burden on the user and the like, and enables a further improvement in operability and user-friendliness.

4. Ultrasonic Transducer Element

Figure 16A:
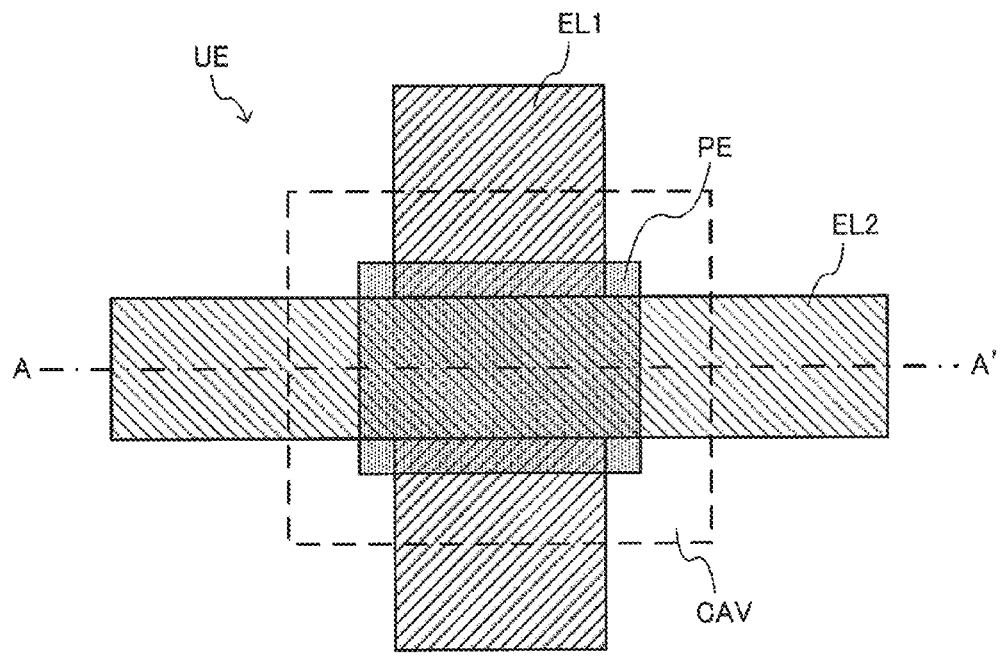
FIGS. 16A and 16B show an example of the configuration of an ultrasonic transducer element.
Figure 16B:
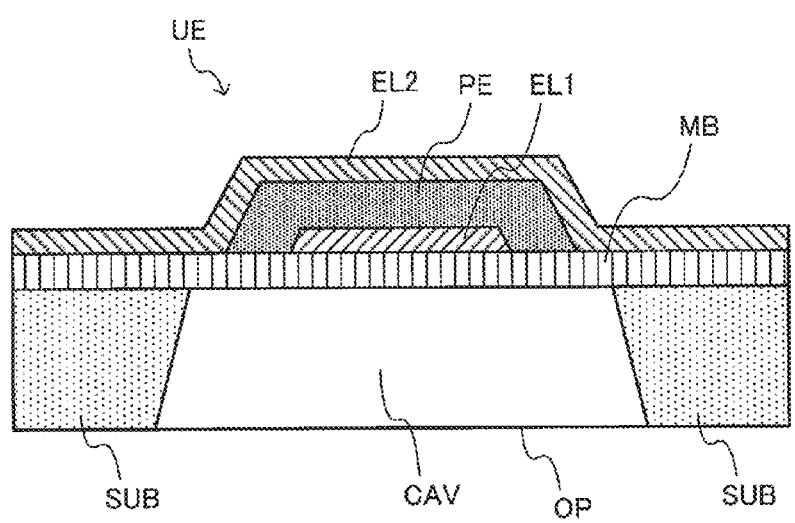

FIGS. 16A and 16B show an example of the configuration of ultrasonic transducer element UE included in the ultrasonic transducer device 100 shown in FIG. 1. In this exemplary configuration, the ultrasonic transducer element UE has a vibrating membrane (membrane, support member) MB and a piezoelectric element unit. The piezoelectric element unit has a first electrode layer (lower electrode) EL1, a piezoelectric film (piezoelectric layer) PE, and a second electrode layer (upper electrode) EL2. Note that the ultrasonic transducer element UE of the present embodiment is not limited to the configuration shown in FIGS. 16A and 16B, and various modifications can be carried out, such as omitting some of the constituent elements, replacing some of the constituent elements with other constituent elements, and adding other constituent elements.

FIG. 16A is a plan view of the ultrasonic transducer element UE formed on a substrate (silicon substrate) SUB, as viewed from a direction perpendicular to the substrate on the element formation face side. FIG. 16B is a cross-sectional diagram showing a cross-section taken along A-A' in FIG. 16A.

The first electrode layer EL1 is formed by a metallic thin film or the like provided on the vibrating membrane MB. This first electrode layer EL1 extends outside the element formation region as shown in FIG. 16A, and may be wiring for connection to an adjacent ultrasonic transducer element UE.

The piezoelectric film PE is formed by a PZT (lead zirconate titanate) thin film, and is provided so as to cover at least a portion of the first electrode layer EL1. Note that the material forming the piezoelectric film PE is not limited to PZT, and it is possible to use lead titanate ($PbTiO_3$), lead zirconate ($PbZrO_3$), lead lanthanum titanate ($(Pb,La)TiO_3$), or the like.

The second electrode layer EL2 is formed by a metallic thin film or the like, and is provided so as to cover at least a portion of the piezoelectric film PE. This second electrode layer EL2 extends outside the element formation region as shown in FIG. 16A, and may be wiring for connection to an adjacent ultrasonic transducer element UE.

The vibrating membrane (membrane) MB has a two-layer structure including an $SiO_2$ thin film and a $ZrO_2$ thin film, for example, and is provided so as to block an opening OP. This vibrating membrane MB supports the piezoelectric film PE and the first and second electrode layers EL1 and EL2, as well as vibrates in accordance with the expansion and contraction of the piezoelectric film PE, and thus can generate ultrasonic waves.

A cavity region CAV is formed by etching the underside of the silicon substrate SUB (face without the element formed thereon) using reactive ion etching (RIE) or the like. Ultrasonic waves are emitted from the opening OP of the cavity region CAV.

The lower electrode of the ultrasonic transducer element UE is formed by the first electrode layer EL1, and the upper electrode is formed by the second electrode layer EL2. Specifically, the portion of the first electrode layer EL1 that is covered by the piezoelectric film PE forms the lower electrode, and the portion of the second electrode layer EL2 that covers the piezoelectric film PE forms the upper electrode. In other words, the piezoelectric film PE is provided so as to be sandwiched between the lower electrode and the upper electrode.

The piezoelectric film PE expands and contracts in the in-plane direction when a voltage is applied between the lower electrode and the upper electrode, that is to say, between the first electrode layer EL1 and the second electrode layer EL2. One of the faces of the piezoelectric film PE is connected to the vibrating membrane MB via the first electrode layer EL1, and the second electrode layer EL2 is formed on the other face, but no other layer is formed on the second electrode layer EL2. For this reason, the vibrating membrane MB side of the piezoelectric film PE does not readily expand and contract, whereas the second electrode layer EL2 side readily expands and contracts. Accordingly, when a voltage is applied to the piezoelectric film PE, it undergoes flexure so as to bulge toward the cavity region CAV side, and thus it causes the vibrating membrane MB to undergo flexure. The vibrating membrane MB vibrates in the film thickness direction due to applying an alternating voltage to the piezoelectric film PE, and ultrasonic waves are emitted from the opening OP due to this vibration of the vibrating membrane MB. The voltage (drive voltage) applied to the piezoelectric film PE is 10 V to 30 V from peak to peak, for example, and the frequency is 1 MHz to 10 MHz, for example.

The ultrasonic transducer element UE also functions as a reception element for receiving ultrasonic echoes when the emitted ultrasonic waves are reflected by the object and return. The vibrating membrane MB vibrates due to the ultrasonic echoing, stress is applied to the piezoelectric film PE due to this vibration, and thus a voltage is generated between the lower electrode and the upper electrode. This voltage can be extracted as a reception signal.

5. Ultrasonic Transducer Device

Figure 17:
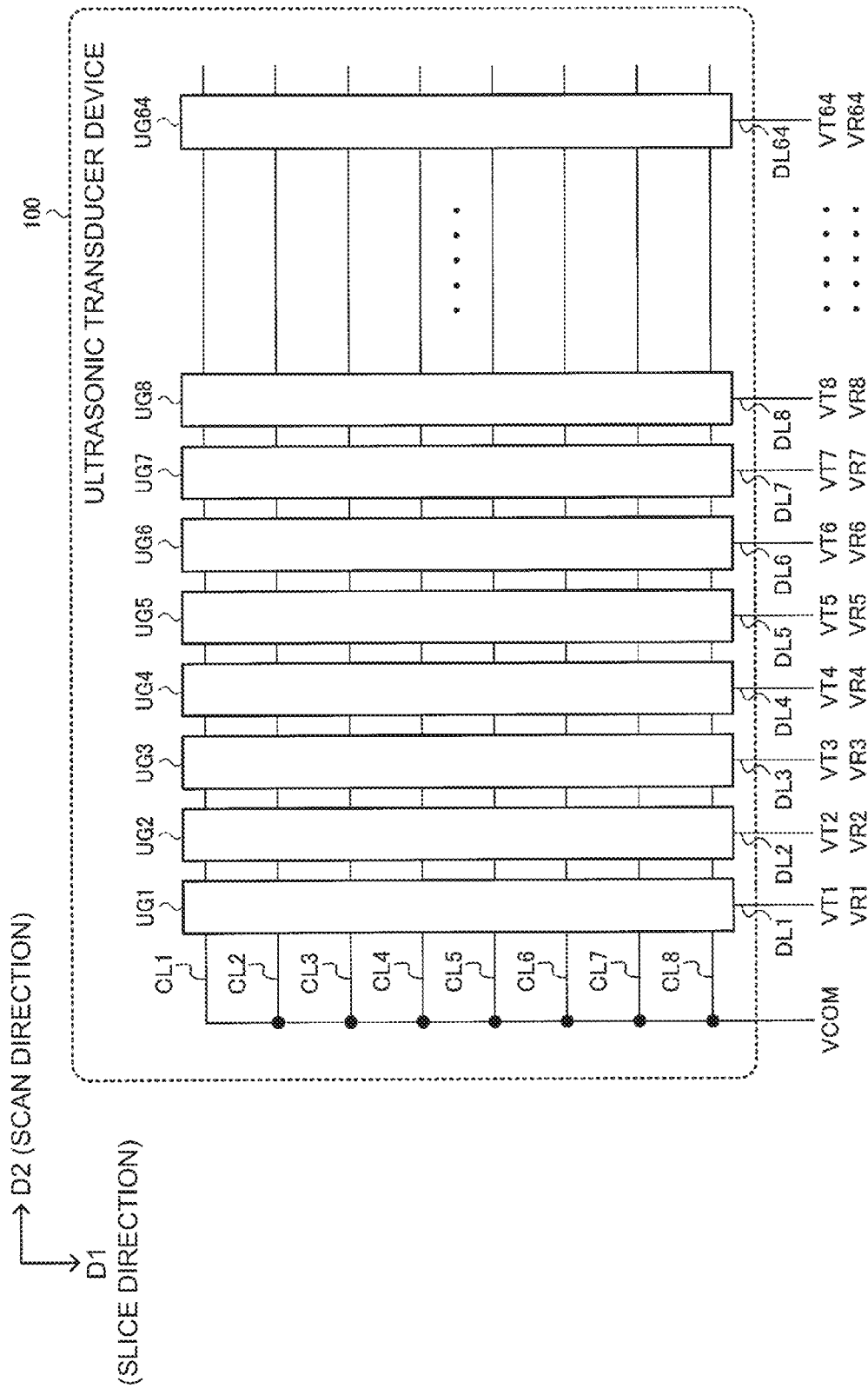
FIG. 17 shows an example of the configuration of the ultrasonic transducer device.

FIG. 17 shows an example of the configuration of the ultrasonic transducer device 100 (element chip). In this exemplary configuration, the ultrasonic transducer device 100 includes ultrasonic transducer element groups UG1 to UG64, driving electrode lines DL1 to DL64 (in a broad sense, 1st to n-th driving electrode lines, where n is an integer greater than or equal to 2), and common electrode lines CL1 to CL8 (in a broad sense, 1st to m-th common electrode lines, where m is an integer greater than or equal to 2). Note that the number of driving electrode lines (n) and the number of common electrode lines (m) are not limited to the numbers shown in FIG. 17.

The ultrasonic transducer element groups UG1 to UG64 are arranged in 64 columns along the second direction D2 (scan direction). The ultrasonic transducer element groups UG1 to UG64 each have multiple ultrasonic transducer elements arranged along the first direction D1 (slice direction).

Figure 18A:
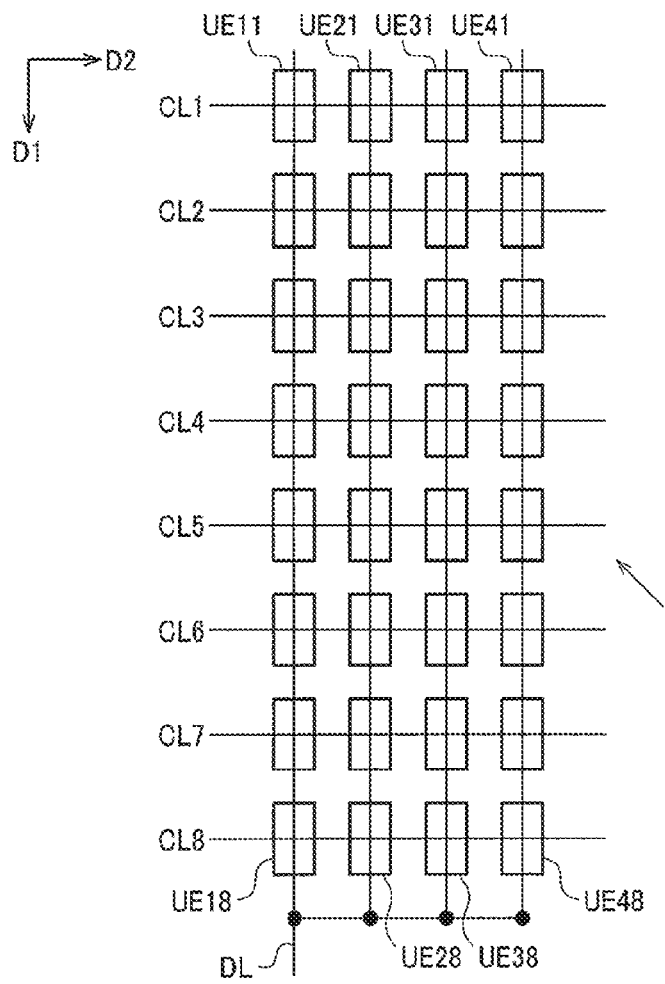
FIGS. 18A and 18B show an example of the configuration of a group of ultrasonic transducer elements provided in correspondence with each channel.

FIG. 18A shows an example of an ultrasonic transducer element group (UG1 to UG64). In FIG. 18A, the ultrasonic transducer element group UG is constituted by first to fourth element columns. The first element column is constituted by the ultrasonic transducer elements UE11 to UE18 arranged along the first direction D1, and the second element column is constituted by the ultrasonic transducer elements UE21 to UE28 arranged along the first direction D1. The same follows for the third element column (UE31 to UE38) and the fourth element column (UE41 to UE48). These first to fourth element columns are connected in common to a driving electrode line DL (DL1 to DL64). Also, the common electrode lines CL1 to CL8 are connected to the ultrasonic transducer elements in the first to fourth element columns.

Figure 18B:
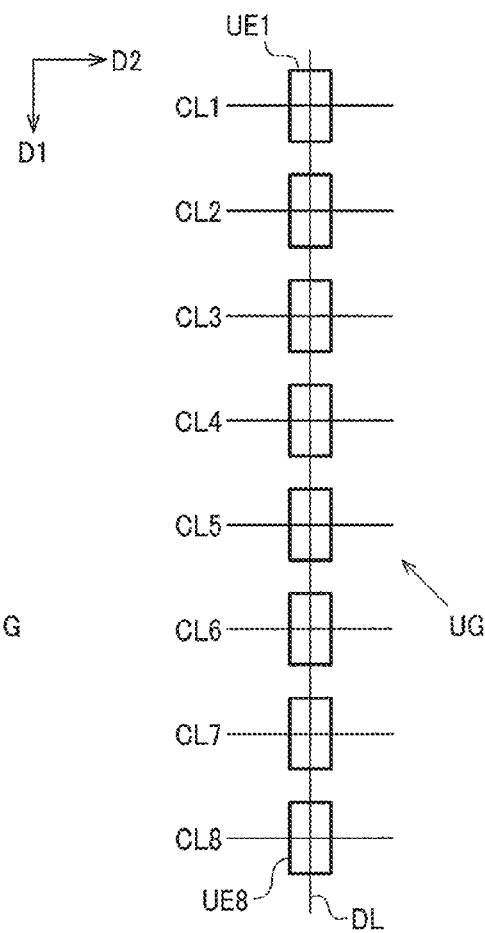

The ultrasonic transducer element group UG in FIG. 18A constitutes one channel of the ultrasonic transducer device. Specifically, the driving electrode line DL corresponds to the driving electrode line of one channel, and the emission signal for one channel is input from the emission circuit to this driving electrode line DL. Also, the reception signal for one channel is output from this driving electrode line DL. Note that the number of element columns that constitute one channel is not limited to being four columns as shown in FIG. 18A, and one channel may be constituted by less than four columns or more than four columns. For example, one channel may be constituted by one element column as shown in FIG. 18B.

As shown in FIG. 17, the driving electrode lines DL1 to DL64 (1st to n-th driving electrode lines) are arranged so as to extend along the first direction D1.

The j-th (j being an integer satisfying $1 \leq j \leq n$) driving electrode line DLj (j-th channel) among the driving electrode lines DL1 to DL64 is connected to the first electrodes (e.g., the lower electrodes) of the ultrasonic transducer elements in the j-th ultrasonic transducer element group UGj.

In the emission period for the emission of ultrasonic waves, emission signals VT1 to VT64 are supplied to the ultrasonic transducer elements via the driving electrode lines DL1 to DL64. Also, in the reception period for receiving ultrasonic echo signals, reception signals VR1 to VR64 are output from the ultrasonic transducer elements via the driving electrode lines DL1 to DL64.

The common electrode lines CL1 to CL8 (1st to m-th common electrode lines) are arranged along the second direction D2. The second electrode of each ultrasonic transducer element is connected to any one of the common electrode lines CL1 to CL8. Specifically, as shown in FIG. 17 for example, the i-th (i being an integer satisfying $1 \leq i \leq m$) common electrode line CL1 among the common electrode lines CL1 to CL8 is connected to the second electrodes (e.g., the upper electrodes) of the ultrasonic transducer elements arranged in the i-th row.

A common voltage VCOM is supplied to the common electrode lines CL1 to CL8. This common voltage VCOM need only be a constant direct current voltage, and does not need to be 0 V, that is to say, ground potential.

In the emission period, the voltage that is the difference between the emission signal voltage and the common voltage is applied to the ultrasonic transducer elements, and ultrasonic waves having a predetermined frequency are emitted.

Note that the arrangement of the ultrasonic transducer elements is not limited to the matrix arrangement shown in FIG. 17, and so-called staggered arrangement or the like may be used.

Also, although FIGS. 16A to 18B show the case where one ultrasonic transducer element is used as both an emission element and a reception element, the present embodiment is not limited to this case. For example, ultrasonic transducer elements serving as emission elements and ultrasonic transducer elements serving as reception elements may be provided separately and arranged in an array.

Note that although various embodiments have been explained in detail above, a person skilled in the art will readily appreciate that it is possible to implement numerous variations and modifications that do not depart substantially from the novel aspects and effect of the invention. Accordingly, all such variations and modifications are also to be included within the scope of the invention. For example, terms that are used within the description or drawings (ultrasonic measuring device, ultrasonic measuring device body, etc.) at least once together with broader terms or alternative synonymous terms (electronic device, electronic device body, etc.) can be replaced by those other terms at other locations as well within the description or drawings. Also the configuration and operation of the ultrasonic measuring device, the ultrasonic transducer device, the ultrasonic transducer element, and the like are not limited to those described in the embodiments, and various modifications are possible.

What is claimed is:

1. An ultrasonic measuring device comprising:
   an ultrasonic transducer device that emits ultrasonic beams along a scanning plane, and receives ultrasonic echoes resulting from the ultrasonic beams; and
   a processing device that performs processing based on a reception signal from the ultrasonic transducer device,
   wherein the processing device includes:
   a data acquisition unit configured to acquire, based on the reception signal, 1st to K-th (K being an integer greater than or equal to 2) A-mode waveform data groups that correspond to 1st to K-th scanning planes in which a direction of the scanning plane of the ultrasonic transducer device relative to a measurement location surface is 1st to K-th directions, respectively;
   a selection unit configured to select a measurement result A-mode waveform data piece based on the 1st to K-th A-mode waveform data groups; and
   a notification control unit configured to generate notification data based on at least one of the measurement result A-mode waveform data piece that was selected and a measurement result A-mode waveform data group that corresponds to the measurement result A-mode waveform data piece, and output the generated notification data,
   the selection unit is further configured to
   obtain 1st to K-th A-mode waveform data pieces from the 1st to K-th A-mode waveform data groups,
   calculate an amplitude at a peak waveform of interest from each of the 1st to K-th A-mode waveform data pieces that were obtained,
   extract an A-mode waveform data piece in which the amplitude at a peak waveform of interest is highest by comparing the calculated amplitudes, and
   select the A-mode waveform data piece in which the amplitude at a peak waveform of interest is highest as the measurement result A-mode waveform data piece.

2. The ultrasonic measuring device according to claim 1, wherein in a case where the selection unit selected an A-mode waveform data piece corresponding to a case where the direction of the scanning plane is an L-th ($1 \leq L \leq K$) direction as the measurement result A-mode waveform data piece, the notification control unit generates the notification data based on at least one of the measurement result A-mode waveform data piece and the measurement result A-mode waveform data group that were acquired when the direction of the scanning plane was the L-th direction, and outputs the generated notification data.

3. The ultrasonic measuring device according to claim 2, wherein the notification control unit generates a B-mode image as the notification data based on the measurement result A-mode waveform data group that was acquired when the direction of the scanning plane was the L-th direction, and outputs the generated B-mode image.

4. The ultrasonic measuring device according to claim 2, wherein the notification control unit generates, as the notification data, an image including a number, a character, or a symbol expressing an ultrasonic measurement result that was obtained when the direction of the scanning plane was the L-th direction, or audio expressing the ultrasonic measurement result, and outputs the image or the audio that was generated.

5. The ultrasonic measuring device according to claim 1, wherein the notification control unit generates a B-mode image as the notification data based on the measurement result A-mode waveform data group that corresponds to the measurement result A-mode waveform data piece that was selected, and outputs the generated B-mode image.

6. The ultrasonic measuring device according to claim 1, wherein the selection unit obtains the 1st to K-th A-mode waveform data pieces from the 1st to K-th A-mode waveform data groups by performing averaging processing for each of the 1st to K-th A-mode waveform data groups or performing selection processing for selecting a representative A-mode waveform data piece from each of the 1st to K-th A-mode waveform data groups.

7. The ultrasonic measuring device according to claim 1, wherein the selection unit performs processing for comparing the amplitude at the peak waveform of interest in an M-th ($1 \leq M < K$) A-mode waveform data piece obtained from an M-th A-mode waveform data group from among the 1st to K-th A-mode waveform data groups with the amplitude at the peak waveform of interest in an (M+1)-th A-mode waveform data piece obtained from an (M+1)-th A-mode waveform data group, and for, out of the M-th A-mode waveform data piece and the (M+1)-th A-mode waveform data piece, selecting and saving the one A-mode waveform data piece for which it was determined that the amplitude at the peak waveform of interest is higher, and deleting the other A-mode waveform data piece and the A-mode waveform data group that corresponds to the other A-mode waveform data piece.

8. The ultrasonic measuring device according to claim 1, comprising:

a correlation data storage unit configured to store correlation data that represents a correlation between the amplitude of the A-mode waveform and depth, wherein the selection unit selects, as the measurement result A-mode waveform data piece, an A-mode waveform data piece for which it was determined that the correlation between the amplitude at the peak waveform of interest and the depth is appropriate based on the correlation data.

9. The ultrasonic measuring device according to claim 1, comprising:

a reference data storage unit configured to store reference A-mode waveform data for a test subject that is to be subjected to ultrasonic measurement, wherein the selection unit obtains 1st to K-th A-mode waveform data pieces from the 1st to K-th A-mode waveform data groups, performs comparison processing for comparing each of the 1st to K-th A-mode waveform data pieces that were obtained with the reference A-mode waveform data stored in the reference data storage unit, and selects the measurement result A-mode waveform from among the 1st to K-th A-mode waveform data pieces.

10. The ultrasonic measuring device according to claim 9, wherein from among the 1st to K-th A-mode waveform data pieces, the selection unit selects an A-mode waveform data piece in which amplitude at a peak waveform of interest is closest to the amplitude at the peak waveform of interest in the reference A-mode waveform data as the measurement result A-mode waveform data piece.

11. The ultrasonic measuring device according to claim 1, comprising:

a guidance instruction unit configured to perform guidance instruction processing for giving a user who is a test subject guidance instruction regarding a direction of the scanning plane of the ultrasonic transducer device.

12. The ultrasonic measuring device according to claim 11, comprising:

a motion sensor that detects motion of the user, wherein the guidance instruction unit performs the guidance instruction processing regarding the direction of the scanning plane based on a motion detection signal from the motion sensor.

13. The ultrasonic measuring device according to claim 1, comprising:

a direction control unit configured to perform direction control for changing a direction of the scanning plane of the ultrasonic transducer device, wherein the data acquisition unit acquires the 1st to K-th A-mode waveform data groups that are obtained as the direction of the scanning plane of the ultrasonic transducer device is changed in accordance with the direction control performed by the direction control unit.

14. The ultrasonic measuring device according to claim 1, wherein the data acquisition unit is further configured to acquire the 1st to K-th A-mode waveform data groups by controlling and changing the direction of the scanning plane of the ultrasonic transducer device relative to the measurement location surface.

15. The ultrasonic measuring device according to claim 1, wherein the selection unit is further configured to select one of the 1st to K-th scanning planes for generating notification data by selecting a measurement result A-mode waveform data piece corresponding to the one of the 1st to K-th scanning planes based on the 1st to K-th A-mode waveform data groups.

16. A non-transitory computer-readable medium with a program for performing processing based on a reception signal from an ultrasonic transducer device that emits ultrasonic beams along a scanning plane and receives ultrasonic echoes resulting from the ultrasonic beams, the program causing a computer to function as:

a data acquisition unit configured to acquire, based on the reception signal, 1st to K-th (K being an integer greater than or equal to 2) A-mode waveform data groups that correspond to 1st to K-th scanning planes in which a direction of the scanning plane of the ultrasonic transducer device relative to a measurement location surface is 1st to K-th directions, respectively;

a selection unit configured to select a measurement result A-mode waveform data piece based on the 1st to K-th A-mode waveform data groups; and a notification control unit configured to generate notification data based on at least one of the measurement result A-mode waveform data piece that was selected and a measurement result A-mode waveform data group that corresponds to the measurement result A-mode waveform data piece, and output the generated notification data, the selection unit is further configured to obtain 1st to K-th A-mode waveform data pieces from the 1st to K-th A-mode waveform data groups, calculate an amplitude at a peak waveform of interest from each of the 1st to K-th A-mode waveform data pieces that were obtained, extract an A-mode waveform data niece in which the amplitude at a peak waveform of interest is highest by comparing the calculated amplitudes, and select the A-mode waveform data piece in which the amplitude at a peak waveform of interest is highest as the measurement result A-mode waveform data piece.

17. A method of controlling an ultrasonic measuring device for performing processing based on a reception signal from an ultrasonic transducer device that emits ultrasonic beams along a scanning plane and receives ultrasonic echoes resulting from the ultrasonic beams, the method comprising:

acquiring, based on the reception signal, 1st to K-th (K being an integer greater than or equal to 2) A-mode waveform data groups that correspond to 1st to K-th scanning planes in which a direction of the scanning plane of the ultrasonic transducer device relative to a measurement location surface is 1st to K-th directions, respectively;

selecting a measurement result A-mode waveform data piece based on the 1st to K-th A-mode waveform data groups; and generating notification data based on at least one of the measurement result A-mode waveform data piece that was selected and a measurement result A-mode waveform data group that corresponds to the measurement result A-mode waveform data piece, and outputting the generated notification data, the selecting including obtaining 1st to K-th A-mode waveform data pieces from the 1st to K-th A-mode waveform data groups, calculating an amplitude at a peak waveform of interest from each of the 1st to K-th A-mode waveform data pieces that were obtained, extracting an A-mode waveform data niece in which the amplitude at a peak waveform of interest is highest by comparing the calculated amplitudes, and selecting the A-mode waveform data piece in which the amplitude at a peak waveform of interest is highest as the measurement result A-mode waveform data piece.

\* \* \* \* \*